United States Patent
Allard et al.

(10) Patent No.: US 9,907,743 B2
(45) Date of Patent: *Mar. 6, 2018

(54) COMPOSITION COMPRISING (2,5-DIAMINOPHENYL)ETHANOL, AN ALKYLPOLYGLUCOSIDE NONIONIC SURFACTANT, AN OXYETHYLENATED SORBITAN ESTER OR A POLYALKOXYLATED OR POLYGLYCEROLATED FATTY ALCOHOL IN A MEDIUM RICH IN FATTY SUBSTANCES, DYEING PROCESS AND DEVICE THEREFOR

(71) Applicant: L'OREAL, Paris (FR)

(72) Inventors: Delphine Allard, Paris (FR); Valerie Nicou, Clichy (FR); Isabelle Rollat, Paris (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/389,411

(22) PCT Filed: Mar. 27, 2013

(86) PCT No.: PCT/EP2013/056628
§ 371 (c)(1),
(2) Date: Sep. 30, 2014

(87) PCT Pub. No.: WO2013/144260
PCT Pub. Date: Oct. 3, 2013

(65) Prior Publication Data
US 2015/0082554 A1 Mar. 26, 2015

Related U.S. Application Data

(60) Provisional application No. 61/640,210, filed on Apr. 30, 2012, provisional application No. 61/700,976, filed on Sep. 14, 2012, provisional application No. 61/700,985, filed on Sep. 14, 2012.

(30) Foreign Application Priority Data

Mar. 30, 2012 (FR) ...................................... 12 52931
Mar. 30, 2012 (FR) ...................................... 12 52945
Mar. 30, 2012 (FR) ...................................... 12 52952

(51) Int. Cl.
| | |
|---|---|
| A61Q 5/10 | (2006.01) |
| A61K 8/92 | (2006.01) |
| A61K 8/31 | (2006.01) |
| A61K 8/41 | (2006.01) |
| A61K 8/60 | (2006.01) |
| A61K 8/86 | (2006.01) |
| A45D 7/04 | (2006.01) |
| A45D 34/00 | (2006.01) |
| A45D 7/00 | (2006.01) |

(52) U.S. Cl.
CPC ................. *A61K 8/92* (2013.01); *A45D 7/04* (2013.01); *A45D 34/00* (2013.01); *A61K 8/31* (2013.01); *A61K 8/411* (2013.01); *A61K 8/604* (2013.01); *A61K 8/86* (2013.01); *A61K 8/922* (2013.01); *A61Q 5/10* (2013.01); *A45D 2007/001* (2013.01); *A61K 2800/882* (2013.01)

(58) Field of Classification Search
CPC ...... A61Q 5/10; A61K 8/92; A61K 2800/882; A45D 34/00; A45D 2007/001
USPC ........................................................... 8/405
See application file for complete search history.

(56) References Cited

U.S. PATENT DOCUMENTS

| | | | |
|---|---|---|---|
| 4,003,699 A | 1/1977 | Rose et al. | |
| 4,137,180 A | 1/1979 | Naik et al. | |
| RE30,199 E | 1/1980 | Rose et al. | |
| 4,874,554 A | 10/1989 | Lange et al. | |
| 5,061,289 A | 10/1991 | Clausen et al. | |
| 5,380,340 A | 1/1995 | Neunhoeffer et al. | |

(Continued)

FOREIGN PATENT DOCUMENTS

| | | |
|---|---|---|
| DE | 23 59 399 A1 | 6/1975 |
| DE | 38 43 892 A1 | 6/1990 |

(Continued)

OTHER PUBLICATIONS

STIC Search Report dated Feb. 5, 2015.*
Todd et al., "Volatile Silicone Fluids for Cosmetics," Cosmetics and Toiletries, vol. 91, Jan. 76, pp. 27-32.
Porter, M.R., "Handbook of Surfactants," published by Blackie & Son (Glasgow and Londaon), 1991, pp. 116-178.
English language abstract of DE 19724334 (Aug. 13, 1998).
English language abstract of DE 19828204 (Oct. 28, 1999).
English language abstract of EP 0727203 (Aug. 21, 1996).
English language abstract of EP 0770375 (May 2, 1997).
English language abstract of EP 1123693 (Aug. 16, 2001).

(Continued)

*Primary Examiner* — Eisa B Elhilo
(74) *Attorney, Agent, or Firm* — The Marbury Law Group, PLLC

(57) ABSTRACT

The present invention relates to a composition for dyeing keratin fibers, in particular human keratin fibers such as the hair, comprising one or more fatty substances, one or more alkylpolyglucoside nonionic surfactants and/or one or more oxyethylenated C8-C30 fatty acid esters of sorbitan, one or more (poly)alkoxylated fatty alcohol(s), and/or one or more (poly)glycerolated fatty alcohol(s); one or more oxidation bases chosen from (2,5-diaminophenyl)ethanol and also acid salts thereof or solvates thereof such as hydrates, optionally one or more couplers, optionally one or more basifying agent(s), one or more chemical oxidizing agent(s), and whose fatty substance content represents in total at least 10% by weight relative to the total weight of the composition and more particularly at least 25% by weight relative to the total weight of the said composition.

20 Claims, No Drawings

(56) References Cited

U.S. PATENT DOCUMENTS

| | | |
|---|---|---|
| 5,534,267 A | 7/1996 | Neunhoeffer et al. |
| 5,599,353 A | 2/1997 | Cotteret et al. |
| 5,663,366 A | 9/1997 | Neunhoeffer et al. |
| 5,716,418 A | 2/1998 | Matzik et al. |
| 5,766,576 A | 6/1998 | Lowe et al. |
| 5,961,667 A | 10/1999 | Doehling et al. |
| 6,099,592 A | 8/2000 | Vidal et al. |
| 6,102,974 A | 8/2000 | Braun |
| 6,224,637 B1 | 5/2001 | Golinski et al. |
| 6,284,003 B1 | 9/2001 | Rose et al. |
| 6,338,741 B1 | 1/2002 | Vidal et al. |
| 6,503,282 B1 | 1/2003 | Braun |
| 6,645,258 B2 | 11/2003 | Vidal et al. |
| 6,730,789 B1 | 5/2004 | Birault et al. |
| 7,918,902 B2 | 4/2011 | Hercouet et al. |
| 7,927,383 B2 | 4/2011 | Hercouet et al. |
| 2002/0010970 A1* | 1/2002 | Cottard et al. ............... 8/405 |
| 2002/0050013 A1 | 5/2002 | Vidal et al. |
| 2003/0019051 A9 | 1/2003 | Vidal et al. |
| 2006/0070191 A1* | 4/2006 | Lang et al. ............... 8/406 |
| 2007/0104672 A1* | 5/2007 | Decoster et al. ......... 424/70.28 |
| 2010/0162492 A1* | 7/2010 | Hercouet et al. .............. 8/416 |
| 2010/0178264 A1 | 7/2010 | Hercouet et al. |
| 2010/0180389 A1 | 7/2010 | Hercouet et al. |

FOREIGN PATENT DOCUMENTS

| | | |
|---|---|---|
| DE | 41 33 957 A1 | 4/1993 |
| DE | 42 27 864 A1 | 2/1994 |
| DE | 195 43 988 A1 | 5/1997 |
| DE | 197 24 334 C1 | 8/1998 |
| DE | 198 28 204 C1 | 10/1999 |
| EP | 0 686 389 A1 | 12/1995 |
| EP | 0 727 203 A1 | 8/1996 |
| EP | 0 770 375 A1 | 5/1997 |
| EP | 0 858 796 A2 | 10/1997 |
| EP | 0 985 406 A1 | 3/2000 |
| EP | 1 123 693 A2 | 8/2001 |
| EP | 2 103 299 A2 | 9/2009 |
| EP | 2 198 832 A1 | 6/2010 |
| EP | 2 198 927 A2 | 6/2010 |
| EP | 2 343 037 A1 | 7/2011 |
| FR | 2733749 A1 | 11/1996 |
| FR | 2801308 A1 | 5/2001 |
| FR | 2886136 A1 | 12/2006 |
| GB | 1026978 A | 4/1966 |
| GB | 1153196 A | 5/1969 |
| JP | 02-019576 | 1/1990 |
| JP | 05-163124 | 6/1993 |
| WO | 94/08969 A1 | 4/1994 |
| WO | 94/08970 A1 | 4/1994 |
| WO | 96/15765 A1 | 5/1996 |
| WO | 98/17233 A1 | 4/1998 |
| WO | 98/19658 A1 | 5/1998 |
| WO | 98/19659 A1 | 5/1998 |
| WO | 98/19660 A1 | 5/1998 |
| WO | 01/51019 A1 | 7/2001 |

OTHER PUBLICATIONS

English language abstract of FR 2886136 (Dec. 1, 2006).
English language abstract of JP 02-019576 (Jan. 23, 1990).
English language abstract of JP 05-163124 (Jun. 29, 1993).

\* cited by examiner

COMPOSITION COMPRISING (2,5-DIAMINOPHENYL)ETHANOL, AN ALKYLPOLYGLUCOSIDE NONIONIC SURFACTANT, AN OXYETHYLENATED SORBITAN ESTER OR A POLYALKOXYLATED OR POLYGLYCEROLATED FATTY ALCOHOL IN A MEDIUM RICH IN FATTY SUBSTANCES, DYEING PROCESS AND DEVICE THEREFOR

CROSS REFERENCE TO RELATED APPLICATIONS

This is a national stage application of PCT/EP2013/056628, filed internationally on Mar. 27, 2013, which claims priority to U.S. Provisional Application No. 61/640,210, filed on Apr. 30, 2012; 61/700,976 filed on Sep. 14, 2012; and 61/700,985 filed on Sep. 14, 2012, as well as French Application Nos. 1252945, 1252952, and 1252931, all filed on Mar. 30, 2012, all of which are incorporated herein by their entireties.

The present invention relates to a composition for dyeing keratin fibres, in particular human keratin fibres such as the hair, comprising a) one or more fatty substances, which are preferably non-silicone liquids, b) one or more alkylpolyglucoside nonionic surfactants, one or more oxyethylenated sorbitan esters, one or more (poly)alkoxylated alcohols and/or one or more (poly)glycerolated alcohols, c) (2,5-diaminophenyl)ethanol and also acid salts thereof or solvates thereof, d) optionally one or more couplers, e) optionally one or more basifying agents, f) one or more chemical oxidizing agents such as hydrogen peroxide, and whose fatty substance content represents in total at least 20% by weight, particularly at least 25% by weight, even more particularly at least 30% by weight, more preferentially at least 40% by weight and even more preferentially at least 50% by weight relative to the total weight of the composition.

The invention also relates to a dyeing process using the said composition, and to a multi-compartment device that is suitable for using the said dye composition.

The present invention relates to the field of dyeing keratin fibres and more particularly to the field of hair dyeing.

Many people have sought for a long time to modify the colour of their hair and in particular to mask their grey hair.

One of the dyeing methods is "permanent" or oxidation dyeing, which uses dyeing compositions containing oxidation dye precursors, generally known as oxidation bases. These oxidation bases are colourless or weakly coloured compounds which, in combination with oxidizing products, can give rise to coloured compounds by an oxidative condensation process.

It is also known that the shades obtained with these oxidation bases may be varied by combining them with couplers or colouration modifiers, the latter being chosen especially from aromatic meta-diamines, meta-aminophenols, meta-diphenols and certain heterocyclic compounds such as indole compounds. The variety of the molecules used as oxidation bases and couplers allows a rich palette of colours to be obtained.

It is also possible to use direct dyes in order especially to provide glints to the colouration obtained. These direct dyes are coloured and colouring molecules that have an affinity for the fibres. Examples that may be mentioned include nitrobenzene, anthraquinone, nitropyridine, azo, xanthene, acridine, azine and triarylmethane direct dyes.

Permanent dyeing processes thus consist in using, with the dye composition, an aqueous composition comprising at least one oxidizing agent, under alkaline pH conditions in the vast majority of cases. The role of this oxidizing agent is, at least partly, to degrade the melanin of the hair, which, depending on the nature of the oxidizing agent present, leads to more or less pronounced lightening of the fibres. The oxidizing agent used is generally hydrogen peroxide.

One of the difficulties encountered during the implementation of the dyeing processes of the prior art arises from the fact that they are carried out under alkaline conditions and that the basifying agents most commonly used are aqueous ammonia and amines. Specifically, the basifying agent makes it possible to adjust the pH of the composition to an alkaline pH to enable activation of the oxidizing agent. In addition, this basifying agent causes swelling of the keratin fibre, with raising of the scales, which promotes the penetration of the oxidizing agent, and also of the dyes, if they are present, essentially oxidation dyes, into the fibre, and thus increases the efficacy of the dyeing or lightening reaction.

However, these basifying agents, and especially aqueous ammonia, have the drawback of causing the user discomfort due to their strong characteristic odour.

In particular, not only may the user be inconvenienced by the odour given off by these basifying agents, but also may be confronted with greater risks of intolerance, for instance irritation of the scalp, which is especially reflected by stinging.

It is also important to obtain colourations that are satisfactorily light-fast. However, the use of certain couplers such as meta-phenylenediamines, for example, induces degradation caused by sunlight.

Moreover, it has been proposed in oxidation dyeing to use an oxidation base of (2,5-diaminophenyl)ethanol type (EP 0 858 796). Colorations that use this oxidation base are also known, especially combined with particular acids such as diethylenetriaminepenta(methylene)phosphonic acid (EP 2 103 299) or with chlorinated bases or chlorinated couplers such as 2-amino-6-chloro-4-nitrophenol, 2,6-dichloro-4-aminophenol, 2-chloro-6-ethylamino-4-nitrophenol 3-amino-5-chloroaniline, 2-chloro-4-aminophenol or 2-chloro-6-methyl-3-aminophenol (WO 98/17233, WO 98/19658, WO 98/19659, WO 98/19660, EP 0 985 406, EP 0 727 203, DE 19828204, DE 19724334 or WO 96/15765), or with couplers such as 3-(2,4-diaminophenoxy)-1-propanol (WO 2001/051019). However, these combinations of bases, couplers and acids produce colours that are not always satisfactory, whose dyeing power is limited or even insufficient to ensure in particular suitable coverage of grey hair and/or which show excessive selectivity of the colouration between the root and the end and/or insufficient fastness with respect to external attacking factors such as light, shampoos, inclement weather, etc. In addition, none of these documents describes a dye composition comprising a large amount of fatty substances, in particular of oil.

One of the objects of the present invention is thus to propose compositions for dyeing human keratin fibres such as the hair, which do not have the drawbacks of the existing compositions.

In particular, the composition according to the invention in the presence of a chemical oxidizing agent makes it possible to obtain colours that are satisfactory, especially in terms of power in general, but also with sufficient coverage or build-up of the colour at the root of the hair, which makes it possible to avoid a "root" effect of the colouration. The colourations obtained are also sparingly selective. Finally, it is also possible to obtain colours that are very light-fast.

Furthermore, the invention makes it possible to achieve substantial degrees of lightening while at the same time colouring, without using persalts or increasing the amount of chemical oxidizing agent or of basifying agent.

These aims and others are achieved by the present invention, one subject of which is thus a cosmetic composition for dyeing keratin fibres, in particular human keratin fibres such as the hair, comprising:

a) one or more fatty substances;

b) one or more alkyl(poly)glucoside nonionic surfactants and/or one or more oxyethylenated $C_8$ to $C_{30}$ fatty acid ester(s) of sorbitan and/or one or more (poly)alkoxylated alcohols and/or one or more (poly)glycerolated alcohols;

c) one or more oxidation base(s) chosen from (2,5-diaminophenyl)ethanol, and also acid salts thereof or solvates thereof such as hydrates;

d) optionally one or more coupler(s);

e) optionally one or more basifying agent(s);

f) one or more chemical oxidizing agent(s); and the fatty substance content representing in total at least 20% by weight relative to the total weight of the composition, preferably at least 25% by weight, more preferably at least 30% by weight, better still at least 40% by weight and even better still at least 50% by weight, relative to the total weight of the composition.

A subject of the present invention is also a process for dyeing keratin fibres, in particular human keratin fibres such as the hair, in which the dye composition according to the invention is applied to the said fibres.

The invention also relates to a multi-compartment device for using the composition according to the invention.

Thus, the use of the dye composition according to the invention leads to powerful, intense, chromatic and/or sparingly selective colourations, i.e. colourations that are uniform along the fibre.

The dyeing process of the invention also makes it possible to cover keratin fibres particularly well at their root, especially down to three centimeters from the base of the said fibres. Moreover, the colours obtained after treating the fibres remain stable, in particular with respect to light.

The invention also makes it possible to reduce the amounts of active agents of the invention such as the dyes and/or basifying agents and/or oxidizing agents.

Moreover, the process according to the invention makes it possible to use compositions that are less malodorous when they are applied to the hair or being prepared.

Other characteristics and advantages of the invention will emerge more clearly on reading the description and the examples that follow.

In the text herein below, and unless otherwise indicated, the limits of a range of values are included in that range.

The human keratin fibres treated via the process according to the invention are preferably the hair.

The expression "at least one" is equivalent to the expression "one or more".

a) Fatty Substances

As has been mentioned, the composition according to the invention comprises a) one or more fatty substances, preferably fatty substances that are liquid at room temperature (25° C.) and at atmospheric pressure.

The term "fatty substance" means an organic compound that is insoluble in water at ordinary temperature (25° C.) and at atmospheric pressure (760 mmHg) (solubility of less than 5%, preferably less than 1% and even more preferentially less than 0.1%). They have in their structure at least one hydrocarbon-based chain containing at least 6 carbon atoms or a sequence of at least two siloxane groups. In addition, the fatty substances are generally soluble in organic solvents under the same temperature and pressure conditions, for instance chloroform, dichloromethane, carbon tetrachloride, ethanol, benzene, toluene, tetrahydrofuran (THF), liquid petroleum jelly or decamethylcyclopentasiloxane.

Preferably, the fatty substances of the invention do not contain any salified or unsalified carboxylic acid groups (—C(O)OH or —C(O)O—). In particular, the fatty substances of the invention are neither polyoxyalkylenated nor polyglycerolated.

Preferably, the fatty substances used in the composition according to the invention are non-silicone oils.

The term "oil" means a "fatty substance" that is liquid at ambient temperature (25° C.) and at atmospheric pressure (760 mmHg).

The term "non-silicone oil" means an oil not containing any silicon atoms (Si) and the term "silicone oil" means an oil containing at least one silicon atom.

In other words, the fatty substance(s) are preferably non-silicone liquid fatty substances.

More particularly, the fatty substances are chosen from C6-C16 hydrocarbons, hydrocarbons containing more than 16 carbon atoms, non-silicone oils of animal origin, plant oils of triglyceride type, synthetic triglycerides, fluoro oils, fatty alcohols, esters of fatty acids and/or of fatty alcohols other than triglycerides and plant waxes, non-silicone waxes and silicones.

It is recalled that, for the purposes of the invention, the fatty alcohols, fatty esters and fatty acids more particularly contain one or more linear or branched, saturated or unsaturated hydrocarbon-based groups comprising 6 to 30 carbon atoms, optionally substituted, in particular, with one or more hydroxyl groups (in particular 1 to 4). If they are unsaturated, these compounds may comprise one to three conjugated or unconjugated carbon-carbon double bonds.

As regards the $C_6$-$C_{16}$ hydrocarbons, they are linear, branched or optionally cyclic, and are preferably alkanes. Examples that may be mentioned include hexane, dodecane and isoparaffins such as isohexadecane and isodecane.

A hydrocarbon-based oil of animal origin that may be mentioned is perhydrosqualene.

The triglyceride oils of plant or synthetic origin are preferably chosen from liquid fatty acid triglycerides containing from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, sunflower oil, castor oil, avocado oil, caprylic/capric acid triglycerides, for instance those sold by the company Stéarineries Dubois or those sold under the names Miglyol® 810, 812 and 818 by the company Dynamit Nobel, jojoba oil and shea butter oil.

The linear or branched hydrocarbons of inorganic or synthetic origin containing more than 16 carbon atoms are preferably chosen from liquid paraffins, petroleum jelly, liquid petroleum jelly, polydecenes and hydrogenated polyisobutene such as Parleam®.

The fluoro oils may be chosen from perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The fatty alcohols that may be used in the composition according to the invention are saturated or unsaturated, linear or branched, and comprise from 6 to 30 carbon atoms and more particularly from 8 to 30 carbon atoms. Mention may be made, for example, of cetyl alcohol, stearyl alcohol and the mixture thereof (cetylstearyl alcohol), octyldodecanol, 2-butyloctanol, 2-hexyldecanol, 2-undecylpentadecanol, oleyl alcohol or linoleyl alcohol.

The wax(es) that may be used in the cosmetic composition according to the invention are chosen especially from carnauba wax, candelilla wax, esparto grass wax, paraffin wax, ozokerite, plant waxes, for instance olive wax, rice wax, hydrogenated jojoba wax or the absolute waxes of flowers such as the essential wax of blackcurrant blossom sold by the company Bertin (France), animal waxes, for instance beeswaxes, or modified beeswaxes (cerabellina); other waxes or waxy starting materials that may be used according to the invention are especially marine waxes such as the product sold by the company Sophim under the reference M82, and polyethylene waxes or polyolefin waxes in general.

As regards the esters of fatty acids and/or of fatty alcohols, which are advantageously different from the triglycerides mentioned above, mention may be made in particular of esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total carbon number of the esters more particularly being greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononanoate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate.

Still within the context of this variant, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

Mention may in particular be made of: diethyl sebacate; diisopropyl sebacate; diisopropyl adipate; di(n-propyl) adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, it is preferred to use ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate and isononyl isononanoate or cetyl octanoate.

The composition may also comprise, as fatty ester, sugar esters and diesters of $C_6$-$C_{30}$ and preferably $C_{12}$-$C_{22}$ fatty acids. It is recalled that the term "sugar" is understood to mean oxygen-bearing hydrocarbon-based compounds that contain several alcohol functions, with or without aldehyde or ketone functions, and that comprise at least 4 carbon atoms. These sugars can be monosaccharides, oligosaccharides or polysaccharides.

Mention may be made, as suitable sugars, for example, of sucrose (or saccharose), glucose, galactose, ribose, fucose, maltose, fructose, mannose, arabinose, xylose and lactose, and derivatives thereof, in particular alkyl derivatives, such as methyl derivatives, for instance methylglucose.

The sugar esters of fatty acids may be chosen in particular from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may comprise one to three conjugated or unconjugated carbon-carbon double bonds.

The esters according to this variant can also be chosen from mono-, di-, tri- and tetraesters, polyesters, and mixtures thereof.

These esters can, for example, be oleates, laurates, palmitates, myristates, behenates, cocoates, stearates, linoleates, linolenates, caprates, arachidonates or mixtures thereof, such as, in particular, oleate/palmitate, oleate/stearate or palmitate/stearate mixed esters.

More particularly, use is made of monoesters and diesters and in particular mono- or di-oleate, -stearate, -behenate, -oleate/palmitate, -linoleate, -linolenate or -oleate/stearate of sucrose, of glucose or of methylglucose.

An example that may be mentioned is the product sold under the name Glucate® DO by the company Amerchol, which is a methylglucose dioleate.

Examples of esters or mixtures of esters of sugar and of fatty acid that may also be mentioned include:
  the products sold under the names F160, F140, F110, F90, F70 and SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose mono laurate;
  the products sold under the name Ryoto Sugar Esters, for example referenced B370 and corresponding to sucrose behenate formed from 20% monoester and 80% diester-triester-polyester;
  the sucrose monopalmitate/stearate-dipalmitate/stearate sold by Goldschmidt under the name Tegosoft® PSE.

The silicones that may be used in accordance with the invention may be in the form of oils, waxes, resins or gums.

Preferably, the silicone is chosen from polydialkylsiloxanes, in particular polydimethylsiloxanes (PDMSs), and organomodified polysiloxanes comprising at least one functional group chosen from amino groups, aryl groups and alkoxy groups.

Organopolysiloxanes are defined in greater detail in Walter Noll's Chemistry and Technology of Silicones (1968), Academic Press. They may be volatile or non-volatile.

When they are volatile, the silicones are more particularly chosen from those having a boiling point of between 60° C. and 260° C., and more particularly still from:

(i) cyclic polydialkylsiloxanes containing from 3 to 7 and preferably from 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, and Silbione® 70045 V5 by Rhodia, and mixtures thereof.

Mention may also be made of cyclocopolymers of the dimethylsiloxane/methylalkylsiloxane type, such as Volatile Silicone® FZ 3109 sold by the company Union Carbide, of formula:

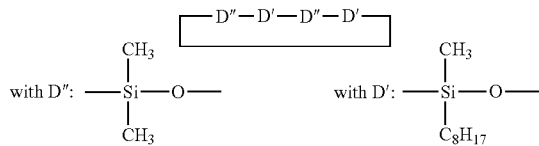

Mention may also be made of mixtures of cyclic polydialkylsiloxanes with organosilicon compounds, such as the mixture of octamethylcyclotetrasiloxane and tetra(trimethylsilyl)pentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing 2 to 9 silicon atoms and having a viscosity of less than or equal to $5 \times 10^{-6}$ m$^2$/s at 25° C. An example is decamethyltetrasiloxane sold in particular under the name SH 200 by the company Toray Silicone. Silicones coming within this category are also described in the paper published in Cosmetics and Toiletries, Vol. 91, January 76, pp. 27-32, Todd & Byers, "Volatile Silicone Fluids for Cosmetics".

Use is preferably made of non-volatile polydialkylsiloxanes, polydialkylsiloxane gums and resins, polyorganosiloxanes modified with the organofunctional groups above, and mixtures thereof.

These silicones are more particularly chosen from polydialkylsiloxanes, among which mention may be made mainly of polydimethylsiloxanes having trimethylsilyl end groups. The viscosity of the silicones is measured at 25° C. according to Standard ASTM 445 Appendix C.

Mention may be made, among these polydialkylsiloxanes, without implied limitation, of the following commercial products:

the Silbione® oils of the 47 and 70 047 series or the Mirasil® oils sold by Rhodia, such as, for example, the oil 70 047 V 500 000;

the oils of the Mirasil® series sold by Rhodia;

the oils of the 200 series from the company Dow Corning, such as DC200 with a viscosity of 60 000 mm$^2$/s;

the Viscasil® oils from General Electric and certain oils of the SF series (SF 96, SF 18) from General Electric.

Mention may also be made of polydimethylsiloxanes having dimethylsilanol end groups known under the name dimethiconol (CTFA), such as the oils of series 48 from the company Rhodia.

In this category of polydialkylsiloxanes, mention may also be made of the products sold under the names Abil Wax® 9800 and 9801 by the company Goldschmidt, which are polydi($C_1$-$C_{20}$)alkylsiloxanes.

The silicone gums that may be used in accordance with the invention are in particular polydialkylsiloxanes and preferably polydimethylsiloxanes with high number-average molecular weights of between 200 000 and 1 000 000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane, tridecane or their mixtures.

Products which can be used more particularly in accordance with the invention are mixtures such as:

the mixtures formed from a polydimethylsiloxane hydroxylated at the chain end, or dimethiconol (CTFA), and from a cyclic polydimethylsiloxane, also known as cyclomethicone (CTFA), such as the product Q2 1401 sold by Dow Corning;

the mixtures of a polydimethylsiloxane gum and of a cyclic silicone, such as the product SF 1214 Silicone Fluid from General Electric; this product is an SF 30 gum corresponding to a dimethicone, having a number-average molecular weight of 500 000, dissolved in the oil SF 1202 Silicone Fluid corresponding to decamethylcyclopentasiloxane;

the mixtures of two PDMSs with different viscosities, and more particularly of a PDMS gum and a PDMS oil, such as the product SF 1236 from General Electric. The product SF 1236 is a mixture of a gum SE 30 defined above, with a viscosity of 20 m$^2$/s, and of an oil SF 96 with a viscosity of $5 \times 10^{-6}$ m$^2$/s. This product preferably comprises 15% of gum SE 30 and 85% of an oil SF 96.

The organopolysiloxane resins that may be used in accordance with the invention are crosslinked siloxane systems containing the following units:

$R_2SiO_{2/2}$, $R_3SiO_{1/2}$, $RSiO_{3/2}$ and $SiO_{4/2}$, in which R represents an alkyl containing 1 to 16 carbon atoms. Among these products, those that are particularly preferred are those in which R denotes a $C_1$-$C_4$ lower alkyl group, more particularly methyl.

Mention may be made, among these resins, of the product sold under the name Dow Corning 593 or those sold under the names Silicone Fluid SS 4230 and SS 4267 by General Electric, which are silicones of dimethyl/trimethylsiloxane structure.

Mention may also be made of the resins of the trimethylsiloxysilicate type, sold especially under the names X22-4914, X21-5034 and X21-5037 by the company Shin-Etsu.

The organomodified silicones that can be used in accordance with the invention are silicones as defined above and comprising in their structure one or more organofunctional group(s) attached via a hydrocarbon-based group.

The organomodified silicones may be polydiarylsiloxanes, in particular polydiphenylsiloxanes, and polyalkylarylsiloxanes functionalized with the organofunctional groups mentioned previously.

The polyalkylarylsiloxanes are particularly chosen from linear and/or branched polydimethyl/methylphenylsiloxanes and polydimethyl/diphenylsiloxanes with a viscosity ranging from $1 \times 10^{-5}$ to $5 \times 10^{-2}$ m$^2$/s at 25° C.

Among these polyalkylarylsiloxanes, examples that may be mentioned include the products sold under the following names:

Silbione® oils of the 70 641 series from Rhodia;

the oils of the Rhodorsil® 70 633 and 763 series from Rhodia;

the oil Dow Corning 556 Cosmetic Grade Fluid from Dow Corning;

the silicones of the PK series from Bayer, such as the product PK20;

the silicones of the PN and PH series from Bayer, such as the products PN1000 and PH1000;

certain oils of the SF series from General Electric, such as SF 1023, SF 1154, SF 1250 and SF 1265.

Mention may also be made, among the organomodified silicones, of polyorganosiloxanes comprising:

substituted or unsubstituted amino groups, such as the products sold under the names GP 4 Silicone Fluid and GP 7100 by Genesee or the products sold under the names Q2 8220 and Dow Corning 929 or 939 by the company Dow Corning. The substituted amino groups are, in particular, $C_1$-$C_4$ aminoalkyl groups;

alkoxylated groups, such as the product sold under the name Silicone Copolymer F-755 by SWS Silicones, and Abil Wax® 2428, 2434 and 2440 by the company Goldschmidt.

Preferably, the fatty substances used in the dye composition according to the invention are non-silicone.

More particularly, the fatty substances are chosen from compounds that are liquid or pasty at room temperature (25° C.) and at atmospheric pressure.

Preferably, the fatty substance is a compound that is liquid at a temperature of 25° C. and at atmospheric pressure.

Even more preferentially, the fatty substances used in the dye composition according to the invention are liquid and non-silicone.

The fatty substances are advantageously chosen from $C_6$-$C_{16}$ hydrocarbons, hydrocarbons containing more than 16 carbon atoms, triglycerides, fatty alcohols, esters of fatty acids and/or of fatty alcohols other than triglycerides, or mixtures thereof.

Preferably, the fatty substance(s) are chosen from liquid petroleum jelly, polydecenes, liquid fatty alcohols and liquid esters of fatty acids and/or of fatty alcohols, or mixtures thereof.

Even more preferentially, the fatty substances are chosen from liquid petroleum jelly and octyldodecanol.

The composition according to the invention comprises in total at least 20% by weight of fatty substances, which are preferably non-silicone, in particular of oils, preferably non-silicone oils, relative to the total weight of the composition of the invention.

Particularly, the composition according to the invention comprises at least 25% by weight, preferably at least 30% by weight, more preferably at least 40% by weight and even more preferably at least 50% by weight of fatty substances which are preferably non-silicone, in particular of oils, preferably non-silicone oils, relative to the total weight of the composition of the invention.

The composition according to the invention more particularly has a content of fatty substances, which are preferably non-silicone, in particular of oils, preferably non-silicone oils, ranging from 25% to 75% by weight, better still from 30% to 70% by weight and even more advantageously from 30% to 60% by weight relative to the weight of the composition.

b) Alkylpolyglucoside Nonionic Surfactants and/or Oxyethylenated $C_8$ to $C_{30}$ Fatty Acid Esters of Sorbitan and/or Oxyethylenated Sorbitan Esters, and/or (Poly)Alkoxylated Alcohols and/or One or More (Poly)Glycerolated Alcohols According to one particular embodiment of the invention, the ingredient b) represents one or more alkyl(poly)glucoside nonionic surfactants.

The term "alkyl(poly)glycoside" denotes an alkylpolyglycoside or an alkylmonoglycoside, also referred to in the present patent application as alkylglycoside, which may be alkoxylated with one or more alkylene oxide groups that are preferentially of $C_2$-$C_4$.

The alkyl(poly)glycoside nonionic surfactant(s) used, alone or as a mixture, in accordance with the present invention may be represented by formula (I) below:

$$R_1O\text{---}(R_2O)_t(G)_v \qquad (I)$$

in which:

$R_1$ represents a saturated or unsaturated, linear or branched alkyl group comprising from about 8 to 24 carbon atoms, or an alkylphenyl group in which the linear or branched alkyl group comprises from 8 to 24 carbon atoms, $R_2$ represents an alkylene group comprising from about 2 to 4 carbon atoms, G represents a saccharide unit comprising from 5 to 6 carbon atoms, t denotes a value ranging from 0 to 10 and preferably from 0 to 4, and v denotes a value ranging from 1 to 15.

Preferably, the alkyl(poly)glycoside nonionic surfactant(s) correspond to formula (I) in which:

$R_1$ denotes a linear or branched, saturated or unsaturated alkyl group containing from 8 to 18 carbon atoms, G denotes glucose, fructose or galactose, preferably glucose, t denotes a value ranging from 0 to 3 and preferably equal to 0, and $R_2$ and v are as defined previously.

The degree of polymerization of the alkyl(poly)glycoside nonionic surfactant(s) as represented, for example, by the index v in formula (I) ranges on average from 1 to 15 and preferably from 1 to 4. This degree of polymerization more particularly ranges from 1 to 2 and better still from 1.1 to 1.5, on average.

The glycoside bonds between the saccharide units are of 1-6 or 1-4 type and preferably of 1-4 type.

Compounds of formula (I) that may be used in the present invention are especially represented by the products sold by the company Cognis under the names Plantaren® (600 CS/U, 1200 and 2000) or Plantacare® (818, 1200 and 2000). It is also possible to use the products sold by the company SEPPIC under the names Triton CG 110 (or Oramix CG 110) and Triton CG 312 (or Oramix® NS 10), the products sold by the company BASF under the name Lutensol GD 70, or those sold by the company Chem Y under the name AG10 LK.

It is also possible, for example, to use the 1-4 ($C_8$-$C_{16}$) alkylpolyglucoside as an aqueous solution at 53% by weight relative to the total weight of the solution, sold by Cognis under the reference Plantacare® 818 UP.

Preferably, the nonionic surfactant used in the composition according to the invention is the ($C_8$-$C_{10}$)alkylglucoside sold under the name Oramix CG 110 by the company SEPPIC.

The alkyl(poly)glycoside nonionic surfactant(s) may be present in the dye composition according to the invention in contents ranging from 0.1% to 20% by weight, in particular from 1% to 15% by weight and better still from 2% to 10% by weight relative to the total weight of the composition.

According to one particular embodiment the ingredient b) represents one or more oxyethylenated $C_8$ to $C_{30}$ fatty acid esters of sorbitan.

The oxyethylenated $C_8$-$C_{30}$ fatty acid esters of sorbitan may be chosen from oxyethylenated derivatives of $C_{8-30}$ fatty acid monoesters and polyesters of sorbitan, containing from 1 to 50 ethylene oxide units.

Use is preferably made of oxyethylenated derivatives of $C_{12-24}$ fatty acid monoesters and polyesters of sorbitan, containing from 4 to 20 ethylene oxide units.

Such compounds are also known as polysorbates. They are sold, inter alia, under the name Tween by the company Uniqema. Examples that may be mentioned include: sorbitan monolaurate oxyethylenated with 4 OE, sold under the name Tween 21, sorbitan monolaurate oxyethylenated with 20 OE, sold under the name Tween 20, sorbitan monopalmitate oxyethylenated with 20 OE, sold under the name Tween 40, sorbitan monostearate oxyethylenated with 20 OE, sold under the name Tween 60, sorbitan monostearate oxyethylenated with 4 OE, sold under the name Tween 61, sorbitan tristearate oxyethylenated with 20 OE, sold under the name Tween 65, sorbitan monooleate oxyethylenated with 20 OE, sold under the name Tween 80, sorbitan monooleate oxyethylenated with 5 OE, sold under the name Tween 81, sorbitan trioleate oxyethylenated with 20 OE, sold under the name Tween 85.

In the present description, and in a manner known per se, the term "compound with X OE" denotes an oxyethylenated compound comprising X oxyethylene units per molecule.

Preferably, the oxyethylenated fatty acid ester of sorbitan is a saturated fatty acid.

Preferably, the oxyethylenated $C_8$-$C_{30}$ fatty acid ester(s) of sorbitan used in the dye composition according to the invention are chosen from oxyethylenated $C_8$-$C_{14}$ fatty acid ester(s) of sorbitan comprising from 2 to 10 oxyethylene units.

Preferably, the composition according to the invention comprises one or more oxyethylenated $C_{12}$ fatty acid esters of sorbitan comprising from 2 to 10 oxyethylene units and preferably 4 oxyethylene units.

Even more preferably, the composition according to the invention comprises sorbitan monolaurate oxyethylenated with 4 OE. This compound is also known as Polysorbate 21.

The composition according to the invention advantageously comprises a total amount of oxyethylenated $C_8$ to $C_{30}$ fatty acid esters of sorbitan ranging from 0.1% to 20% by weight, preferably ranging from 0.5% to 10% by weight and more preferentially ranging from 1% to 5% by weight relative to the total weight of the composition.

According to a particular embodiment, ingredient b) represents one or more (poly)alkoxylated or (poly)glycerolated fatty alcohols which are saturated or unsaturated ethers. When they are unsaturated, these compounds may preferably comprise from one to three conjugated or unconjugated carbon-carbon double bonds.

The term "alkoxylated" means that the said aliphatic chain of fatty alcohol is interrupted and/or terminated, preferably terminated, with several divalent groups —[O-Alk]$_n$- or -[Alk-O]$_n$— with Alk representing a linear or branched $C_1$-$C_6$, preferably linear $C_1$-$C_4$, alkylene group such as ethylene —CH$_2$—CH$_2$—; and n representing an integer ranging from 1 to 200, preferably from 2 to 150 and even more preferentially from 3 to 100.

The (poly)alkoxylated alcohol(s) are particularly of formula (A1) below:

$$R^a[O\text{-}Alk]_n\text{-}OH \qquad (A1)$$

in which formula (A1):
Alk is as defined previously;
Ra represents a $C_8$-$C_{40}$ and preferably $C_8$-$C_{30}$ linear or branched alkyl or linear or branched alkenyl group optionally substituted with one or more hydroxyl groups; and
n represents an integer ranging from 1 to 200, preferentially from 2 to 150, more particularly from 3 to 100, preferentially between 2 and 50, better still from 8 to 50, more particularly inclusively between 8 and 30 and better still from 15 to 25, such as 20.

Preferably, the composition of the invention comprises one or more (poly)ethoxylated fatty alcohols (corresponding to the compounds of formula (A1) in which the unit Alk denotes an ethylenic group —CH$_2$—CH$_2$—).

The (poly)ethoxylated fatty alcohols that are suitable for use in the invention are more particularly chosen from alcohols comprising from 8 to 40 carbon atoms, preferably from 8 to 30 carbon atoms and more particularly from 12 to 22 carbon atoms.

The (poly)ethoxylated fatty alcohols are more particularly fatty alcohols comprising from 8 to 22 carbon atoms and oxyethylenated with 2 to 30 mol of ethylene oxide (2 to 30 OE). Among these, mention may be made more particularly of lauryl alcohol 2 OE, lauryl alcohol 3 OE, decyl alcohol 3 OE, decyl alcohol 5 OE and oleyl alcohol 20 OE.

More particularly, the fatty alcohol(s) containing 15 to 25 mol of OE may be, for example, oxyethylenated stearyl alcohol 20 OE (Tego Alkanol S20P from Evonik), oxyethylenated (20 OE) oxypropylenated (5 OP) cetyl alcohol (Simulsol PG 558 from SEPPIC), oxyethylenated (20 OE) oleyl alcohol (Brij O20-SO-(MV) from Croda).

Mixtures of these (poly)alkoxylated fatty alcohols may also be used.

As examples of (poly)glycerolated, i.e. monoglycerolated or polyglycerolated, fatty alcohols, use is preferably made of (poly)glycerolated $C_8$-$C_{40}$ alcohols.

In particular, $C_8$-$C_{40}$ (poly)glycerolated alcohols correspond to formula (A2) below:

$$R^b\text{O}\text{—}[CH_2\text{—}CH(CH_2OH)\text{—}O]_m\text{—}H \qquad (A2)$$

in which formula (A3):
$R_b$ represents a linear or branched $C_8$-$C_{40}$ and preferably $C_8$-$C_{30}$ alkyl or alkenyl radical; and
m represents a number ranging from 1 to 30 and preferably from 2 to 10.

As examples of compounds that are suitable in the context of the invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The (poly)alkoxylated or (poly)glycerolated fatty alcohol(s) of the invention may be in the form of a mixture of alcohols in the same respect that the value of m and n represents a statistical value, which means that several species of (poly)alkoxylated or (poly)glycerolated fatty alcohols may coexist in the form of a mixture within the same commercial product.

According to the present invention, the (poly)alkoxylated or (poly)glycerolated, in particular (poly)ethoxylated, fatty alcohol(s) are preferably present in the composition in an amount ranging from 0.1% to 40% by weight, preferably from 0.5% to 25% by weight and better still from 1% to 10% by weight relative to the total weight of the composition.

According to a particularly advantageous embodiment, the ingredient b) is chosen from (poly)alkoxylated alcohols and is more preferentially chosen from (poly)ethoxylated alcohols and even more preferentially from ethoxylated fatty alcohols with from 15 to 25 mol of ethylene oxide.

According to another particular embodiment of the invention, the ingredient b) represents a mixture of one or more alkyl(poly)glucoside nonionic surfactants and of one or more oxyethylenated $C_8$ to $C_{30}$ fatty acid esters of sorbitan and/or one or more (poly)alkoxylated or (poly)glycerolated fatty alcohols. The said mixture is preferably present in the dye composition in an amount ranging from 0.1% to 40% by weight, preferably from 0.5% to 25% by weight and better still from 1% to 10% by weight relative to the total weight of the composition.

The dye composition according to the invention may also contain one or more additional or supplementary different alkyl(poly)glucoside nonionic surfactants, oxyethylenated $C_8$ to $C_{30}$ fatty acid esters of sorbitan, (poly)alkoxylated fatty alcohols or (poly)glycerolated fatty alcohols as defined previously.

According to a particular embodiment of the invention, the additional surfactant(s) are chosen from anionic, cationic, amphoteric or zwitterionic or nonionic surfactants, and preferentially nonionic surfactants, the latter surfactants being different from the alkyl(poly)glycosides of the invention.

The term "anionic surfactant" means a surfactant comprising, as ionic or ionizable groups, only anionic groups. These anionic groups are preferably chosen from the groups —C(O)OH, —C(O)O$^-$, —SO$_3$H, —S(O)$_2$O$^-$, —OS(O)$_2$OH, —OS(O)$_2$O$^-$, —P(O)OH$_2$, —P(O)$_2$O$^-$, —P(O)O$_2^-$, —P(OH)$_2$, =P(O)OH, —P(OH)O$^-$, =P(O)O$^-$, =POH and =PO$^-$, the anionic parts comprising a cationic counterion such as an alkali metal, an alkaline-earth metal or an ammonium.

Mention may be made, as examples of anionic surfactants which can be used in the composition according to the invention, of alkyl sulfates, alkyl ether sulfates, alkylamido ether sulfates, alkylaryl polyether sulfates, monoglyceride sulfates, alkylsulfonates, alkylamidesulfonates, alkylarylsulfonates, α-olefinsulfonates, paraffinsulfonates, alkyl sulfosuccinates, alkyl ether sulfosuccinates, alkylamide sulfosuccinates, alkyl sulfoacetates, acyl sarcosinates, acyl glutamates, alkyl sulfosuccinamates, acyl isethionates and N-acyl taurates, salts of alkyl monoesters of polyglycoside-polycarboxylic acids, acyl lactylates, salts of D-galactosideuronic acids, salts of alkyl ether carboxylic acids, salts of alkylaryl ether carboxylic acids, salts of alkylamido ether carboxylic acids, and the corresponding non-salified forms of all these compounds, the alkyl and acyl groups of all these compounds comprising from 6 to 24 carbon atoms and the aryl group denoting a phenyl group.

These compounds can be oxyethylenated and then preferably comprise from 1 to 50 ethylene oxide units.

The salts of $C_6$-$C_{24}$ alkyl monoesters of polyglycoside-polycarboxylic acids can be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfo succinates.

When the anionic surfactant(s) are in salt form, they may be chosen from alkali metal salts such as the sodium or potassium salt and preferably the sodium salt, ammonium salts, amine salts and in particular amino alcohol salts or alkaline-earth metal salts such as the magnesium salts.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Use is preferably made of alkali metal or alkaline-earth metal salts and in particular of sodium or magnesium salts.

Use is preferably made, among the anionic surfactants mentioned, of ($C_6$-$C_{24}$)alkyl sulfates, ($C_6$-$C_{24}$)alkyl ether sulfates comprising from 2 to 50 ethylene oxide units, in particular in the form of alkali metal, ammonium, amino alcohol and alkaline-earth metal salts, or a mixture of these compounds.

In particular, it is preferable to use ($C_{12}$-$C_{20}$)alkyl sulfates, ($C_{12}$-$C_{20}$)alkyl ether sulfates comprising from 2 to 20 ethylene oxide units, in particular in the form of alkali metal, ammonium, amino alcohol and alkaline-earth metal salts, or a mixture of these compounds. Better still, it is preferred to use sodium lauryl ether sulfate containing 2.2 mol of ethylene oxide.

The cationic surfactant(s) which can be used in the composition according to the invention comprise, for example, salts of optionally polyoxyalkylenated primary, secondary or tertiary fatty amines, quaternary ammonium salts, and mixtures thereof.

Examples of quaternary ammonium salts that may in particular be mentioned include:
those corresponding to the general formula (II) below:

in which formula (II):

$R_8$ to $R_{11}$, which may be identical or different, represent a linear or branched aliphatic group comprising from 1 to 30 carbon atoms, or an aromatic group such as aryl or alkylaryl, it being understood that at least one of the groups $R_8$ to $R_{11}$ comprises from 8 to 30 carbon atoms and preferably from 12 to 24 carbon atoms; and X$^-$ represents an organic or inorganic anionic counterion, such as that chosen from halides, acetates, phosphates, nitrates, ($C_1$-$C_4$)alkyl sulfates, ($C_1$-$C_4$)alkyl or ($C_1$-$C_4$) alkylaryl sulfonates, in particular methyl sulfate and ethyl sulfate.

The aliphatic groups of $R_8$ to $R_{11}$ may also comprise heteroatoms especially such as oxygen, nitrogen, sulfur and halogens.

The aliphatic groups of $R_8$ to $R_{11}$ are chosen, for example, from $C_1$-$C_{30}$ alkyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkyl acetate, $C_1$-$C_{30}$ hydroxyalkyl groups, X$^-$ is an anionic counterion chosen from the group of halides, phosphates, acetates, lactates, ($C_1$-$C_4$)alkyl sulfates, and ($C_1$-$C_4$) alkyl- or ($C_1$-$C_4$)alkylarylsulfonates.

Among the quaternary ammonium salts of formula (II), preference is given firstly to tetraalkylammonium chlorides, for instance dialkyldimethylammonium or alkyltrimethylammonium chlorides in which the alkyl group contains approximately from 12 to 22 carbon atoms, in particular behenyltrimethylammonium chloride, distearyldimethylammonium chloride, cetyltrimethylammonium chloride, benzyldimethylstearylammonium chloride, or else, secondly, distearoylethylhydroxyethylmethylammonium methosulfate, dipalmitoylethylhydroxyethylammonium methosulfate or distearoylethylhydroxyethylammonium methosulfate, or else, lastly, palmitylamidopropyltrimethylammonium chloride or stearamidopropyldimethyl(myristyl acetate)ammonium chloride, sold under the name Ceraphyl® 70 by the company Van Dyk;

quaternary ammonium salts of imidazoline, for instance those of formula (III) below:

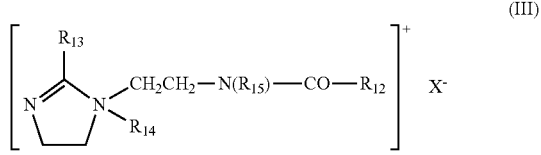

(III)

in which formula (III):

$R_{12}$ represents an alkenyl or alkyl group comprising from 8 to 30 carbon atoms, for example fatty acid derivatives of tallow;

$R_{13}$ represents a hydrogen atom, a $C_1$-$C_4$ alkyl group or an alkenyl or alkyl group comprising from 8 to 30 carbon atoms;

$R_{14}$ represents a $C_1$-$C_4$ alkyl group;

$R_{15}$ represents a hydrogen atom or a $C_1$-$C_4$ alkyl group;

$X^-$ represents an organic or inorganic anionic counterion, such as that chosen from halides, phosphates, acetates, lactates, ($C_1$-$C_4$)alkyl sulfates, ($C_1$-$C_4$)alkyl or ($C_1$-$C_4$) alkylaryl sulfonates.

$R_{12}$ and $R_{13}$ preferably denote a mixture of alkyl or alkenyl groups containing from 12 to 21 carbon atoms, for example tallow fatty acid derivatives, $R_{14}$ denotes a methyl group, and $R_{15}$ denotes a hydrogen atom. Such a product is sold, for example, under the name Rewoquat® W 75 by the company Rewo;

quaternary diammonium or triammonium salts, particularly of formula (IV) below:

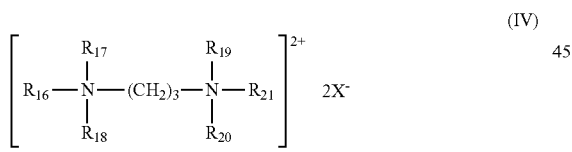

(IV)

in which formula (IV):

$R_{16}$ denotes an alkyl group comprising approximately from 16 to 30 carbon atoms, which is optionally hydroxylated and/or interrupted with one or more oxygen atoms;

$R_{17}$ is chosen from hydrogen, an alkyl group comprising from 1 to 4 carbon atoms or a group $-(CH_2)_3-N^+$ $(R_{16a})(R_{17a})(R_{18a})$, $X^-$;

$R_{16a}$, $R_{17a}$, $R_{18a}$, $R_{18}$, $R_{19}$, $R_{20}$ and $R_{21}$, which may be identical or different, are chosen from hydrogen and an alkyl group comprising from 1 to 4 carbon atoms; and $X^-$, which may be identical or different, represent an organic or inorganic anionic counterion, such as that chosen from halides, acetates, phosphates, nitrates, ($C_1$-$C_4$)alkyl sulfates, ($C_1$-$C_4$)alkyl or ($C_1$-$C_4$)alkylaryl sulfonates, in particular methyl sulfate and ethyl sulfate.

Such compounds are, for example, Finquat CT-P, sold by the company Finetex (Quaternium 89), and Finquat CT, sold by the company Finetex (Quaternium 75);

quaternary ammonium salts containing one or more ester functions, such as those of formula (V) below:

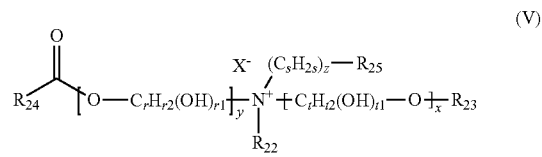

(V)

in which formula (V):

$R_{22}$ is chosen from $C_1$-$C_6$ alkyl groups and $C_1$-$C_6$ hydroxyalkyl or dihydroxyalkyl groups, $R_{23}$ is chosen from:

the group

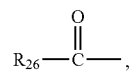

linear or branched, saturated or unsaturated $C_1$-$C_{22}$ hydrocarbon-based groups $R_{27}$, a hydrogen atom, $R_{25}$ is chosen from:

the group

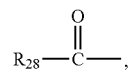

linear or branched, saturated or unsaturated $C_1$-$C_6$ hydrocarbon-based groups $R_{29}$, a hydrogen atom, $R_{24}$, $R_{26}$ and $R_{28}$, which may be identical or different, are selected from linear or branched, saturated or unsaturated $C_7$-$C_{21}$ hydrocarbon-based groups;

r, s and t, which may be identical or different, are integers ranging from 2 to 6, r1 and t1, which may be identical or different, are equal to 0 or 1, with r2+r1=2r and t1+t2=2t, y is an integer ranging from 1 to 10, x and z, which may be identical or different, are integers ranging from 0 to 10, $X^-$ represents an organic or inorganic anionic counterion, with the proviso that the sum x+y+z equals from 1 to 15, that, when x is 0, then $R_{23}$ denotes $R_{27}$ and that, when z is 0, then $R_{25}$ denotes $R_{29}$.

The alkyl groups $R_{22}$ may be linear or branched, and more particularly linear.

Preferably, $R_{22}$ denotes a methyl, ethyl, hydroxyethyl or dihydroxypropyl group, and more particularly a methyl or ethyl group.

Advantageously, the sum x+y+z has a value from 1 to 10.

When $R_{23}$ is an $R_{27}$ hydrocarbon group, it may be long and may contain from 12 to 22 carbon atoms, or may be short and may contain from 1 to 3 carbon atoms.

When $R_{25}$ is an $R_{29}$ hydrocarbon-based group, it preferably contains 1 to 3 carbon atoms.

Advantageously, $R_{24}$, $R_{26}$ and $R_{28}$, which are identical or different, are selected from linear or branched, saturated or unsaturated $C_{11}$-$C_{21}$ hydrocarbon-based groups, and more particularly from linear or branched, saturated or unsaturated $C_{11}$-$C_{21}$ alkyl and alkenyl groups.

Preferably, x and z, which may be identical or different, are equal to 0 or 1.

Advantageously, y is equal to 1.

Preferably, r, s and t, which are identical or different, have values of 2 or 3 and even more particularly are equal to 2.

The anionic counterion $X^-$ is preferably a halide, such as chloride, bromide or iodide; a ($C_1$-$C_4$)alkyl sulfate or a ($C_1$-$C_4$)alkyl- or ($C_1$-$C_4$)alkylarylsulfonate. However, it is possible to use methanesulfonate, phosphate, nitrate, tosylate, an anion derived from an organic acid, such as acetate or lactate, or any other anion that is compatible with the ammonium comprising an ester function.

The anionic counterion $X^-$ is even more particularly chloride, methyl sulfate or ethyl sulfate.

Use is made more particularly in the composition according to the invention of the ammonium salts of formula (V) in which:
$R_{22}$ denotes a methyl or ethyl group,
x and y are equal to 1,
z is equal to 0 or 1,
r, s and t are equal to 2,
$R_{23}$ is chosen from:
the group

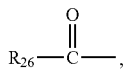

methyl, ethyl or $C_{14}$-$C_{22}$ hydrocarbon-based groups,
a hydrogen atom,
$R_{25}$ is chosen from:
the group

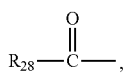

a hydrogen atom,
$R_{24}$, $R_{26}$ and $R_{28}$, which may be identical or different, are chosen from linear or branched, saturated or unsaturated $C_{13}$-$C_{17}$ hydrocarbon-based groups, and preferably from linear or branched, saturated or unsaturated $C_{13}$-$C_{17}$ alkyl and alkenyl groups.

Advantageously, the hydrocarbon radicals are linear.

Among the compounds of formula (V), examples that may be mentioned include salts, especially the chloride or methyl sulfate, of diacyloxyethyldimethylammonium, diacyloxyethylhydroxyethyl-methylammonium, monoacyloxyethyldihydroxyethylmethylammonium, triacyloxyethylmethylammonium or monoacyloxyethylhydroxyethyldimethylammonium, and mixtures thereof. The acyl groups preferably contain from 14 to 18 carbon atoms and originate more particularly from a plant oil, such as palm oil or sunflower oil. When the compound comprises several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with fatty acids or with fatty acid mixtures of plant or animal origin, or by transesterification of the methyl esters thereof. This esterification is followed by a quaternization by means of an alkylating agent, such as an alkyl halide, preferably methyl or ethyl halide, a dialkyl sulfate, preferably dimethyl or diethyl sulfate, methyl methanesulfonate, methyl para-toluenesulfonate, glycol chlorohydrin or glycerol chlorohydrin.

Such compounds are sold, for example, under the names Dehyquart® by the company Henkel, Stepanquat® by the company Stepan, Noxamium® by the company Ceca or Rewoquat® WE 18 by the company Rewo-Witco.

The composition according to the invention may contain, for example, a mixture of quaternary ammonium salts of monoesters, diesters and triesters with a weight majority of diester salts.

Use may also be made of the ammonium salts containing at least one ester function that are described in U.S. Pat. No. 4,874,554 and U.S. Pat. No. 4,137,180.

Use may be made of behenoylhydroxypropyltrimethylammonium chloride, sold by Kao under the name Quatarmin BTC 131.

Preferably, the ammonium salts containing at least one ester function contain two ester functions.

Among the cationic surfactants that may be present in the composition according to the invention, it is more particularly preferred to choose cetyltrimethylammonium, behenyltrimethylammonium and dipalmitoylethylhydroxyethylmethylammonium salts, and mixtures thereof, and more particularly behenyltrimethylammonium chloride, cetyltrimethylammonium chloride and dipalmitoylethylhydroxyethylammonium methosulfate, and mixtures thereof.

Examples of additional nonionic surfactants that may be used in the composition used according to the invention are described, for example, in the "Handbook of Surfactants" by M. R. Porter, published by Blackie & Son (Glasgow and London), 1991, pp 116-178. They are especially chosen from alcohols, α-diols and ($C_1$-$C_{20}$)alkylphenols, these compounds being polyethoxylated, polypropoxylated and/or polyglycerolated, and containing at least one fatty chain comprising, for example, from 8 to 18 carbon atoms, it being possible for the number of ethylene oxide and/or propylene oxide groups to especially range from 2 to 50, and for the number of glycerol groups to especially range from 2 to 30.

Mention may also be made of copolymers of ethylene oxide and propylene oxide, non-oxyethylenated fatty acid esters of sorbitan, fatty acid esters of sucrose, polyoxyalkylenated fatty acid esters, non-oxyalkylenated alkylpolyglycosides, alkylglucoside esters, derivatives of N-alkylglucamine and of N-acylmethylglucamine, aldobionamides and amine oxides.

The term "amphoteric or zwitterionic surfactant" means a surfactant comprising in its structure one or more cationic sites and one or more anionic sites.

The amphoteric or zwitterionic surfactant(s) that can be used in the present invention may especially be optionally quaternized secondary or tertiary aliphatic amine derivatives, in which the aliphatic group is a linear or branched chain comprising from 8 to 22 carbon atoms, the said amine derivatives containing at least one anionic group such as, for example, a carboxylate, sulfonate, sulfate, phosphate or phosphonate group. Among the optionally quaternized secondary or tertiary aliphatic amine derivatives that may be used, as defined above, mention may be made of the compounds of respective structures (A3) and (A4) below:

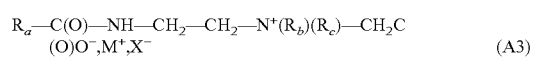

in which formula (A3):
R$_a$ represents a C$_{10}$-C$_{30}$ alkyl or alkenyl group derived from an acid R$_a$—COOH preferably present in hydrolysed coconut oil, or a heptyl, nonyl or undecyl group;
R$_b$ represents a β-hydroxyethyl group; and
R$_c$ represents a carboxymethyl group;
M$^+$ represents a cationic counterion derived from an alkali metal or alkaline-earth metal, such as sodium, an ammonium ion or an ion derived from an organic amine, and
X$^-$ represents an organic or inorganic anionic counterion, such as that chosen from halides, acetates, phosphates, nitrates, (C$_1$-C$_4$)alkyl sulfates, (C$_1$-C$_4$)alkyl- or (C$_1$-C$_4$) alkylarylsulfonates, in particular methyl sulfate and ethyl sulfate; or alternatively M$^+$ and X$^-$ are absent;

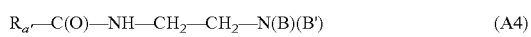

(A4)

in which formula (A4):
B represents the group —CH$_2$—CH$_2$—O—X';
B' represents the group —(CH$_2$)$_z$Y', with z=1 or 2;
X' represents the group —CH$_2$—C(O)OH, —CH$_2$—C(O)OZ', —CH$_2$—CH$_2$—C(O)OH, —CH$_2$—CH$_2$—C(O)OZ', or a hydrogen atom;
Y' represents the group —C(O)OH, —C(O)OZ', —CH$_2$—CH(OH)—SO$_3$H or the group —CH$_2$—CH(OH)—SO$_3$—Z';
Z' represents a cationic counterion derived from an alkali metal or alkaline-earth metal, such as sodium, an ammonium ion or an ion derived from an organic amine;
R$_{a'}$ represents a C$_{10}$-C$_{30}$ alkyl or alkenyl group of an acid R$_{a'}$—C(O)OH preferably present in coconut oil or in hydrolysed linseed oil, an alkyl group, especially of C$_{17}$ and its iso form, or an unsaturated C$_{17}$ group.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid and cocoamphodipropionic acid.

By way of example, mention may be made of the cocoamphodiacetate sold by the company Rhodia under the trade name Miranol® C2M Concentrate.

More particularly, the amphoteric or zwitterionic surfactant(s) are chosen from the betaine surfactants of formula (A5), and also the acid or base salts thereof, and solvates thereof such as hydrates:

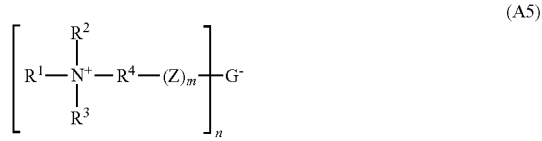

(A5)

in which formula (A5):
R$^1$ denotes a saturated or unsaturated, linear or branched hydrocarbon-based chain, comprising from 6 to 100 carbon atoms and in particular from 6 to 50 carbon atoms, which may be interrupted with one or more heteroatoms, divalent groups, or combinations thereof chosen from —O—, —C(O)— and —N(R)—; with R denoting a hydrogen atom or a C$_1$-C$_4$ alkyl radical, and R$^1$ also possibly being interrupted with an arylene group or terminated with an aryl group;
R$^2$ and R$^3$, which may be identical or different, in particular R$^2$ and R$^3$ are identical, denote a (C$_1$-C$_6$)alkyl group; preferably, R$^2$ and R$^3$ represent a methyl group;
R$^4$ denotes a linear or branched, preferably linear, divalent hydrocarbon-based radical, comprising from 1 to 10 and preferably from 1 to 5 carbon atoms, optionally substituted in particular with one or more hydroxyl groups;
Z denotes a heteroatom or a divalent group chosen from —O— and —N(R)— with R as defined previously,
n denotes a number equal to 1 or 2;
m denotes an integer equal to 0 or 1;
G$^-$ denotes an anionic radical chosen from carboxylates, sulfates, sulfonates, phosphates and phosphonates (*—C(O)—O$^-$, *—S(O)$_2$—O$^-$, *—O—S(O)$_2$—O$^-$, *—P(O)$_2$—O$^-$, *—P(O)—O$_2$$^-$, *—P(OH)—O$^-$, =P(O)—O$^-$ and =P—O$^-$; with "*—" denoting the point of attachment of the anionic radical to the rest of the molecule via Z or R$^4$ when n is 1, and "**=" representing the two points of attachment of the anionic radical via Z or R$^4$ when n is 2);
it being understood that:
when n is 2, the radicals R$^1$R$^2$R$^3$N$^+$—R'—(Z)$_m$— are identical or different, preferably identical; and
the surfactant of formula (A5) being electrically neutral, it may comprise anionic and/or cationic counterions to produce the electrical neutrality of the molecule.

The term "unsaturated" hydrocarbon-based chain means a hydrocarbon-based chain which comprises one or more double bonds and/or one or more triple bonds, the said bonds possibly being conjugated or non-conjugated.

The term "alkyl radical" means a saturated linear or branched hydrocarbon-based radical, preferably of C$_1$-C$_8$.

The term "alkenyl radical" means a linear or branched, preferably C$_2$-C$_8$, hydrocarbon-based radical; which is unsaturated, comprising one or more conjugated or non-conjugated double bonds.

The term "alkoxy radical" means an alkyl-oxy radical for which the alkyl radical is a linear or branched C$_1$-C$_{16}$ and preferentially C$_1$-C$_8$ hydrocarbon-based radical.

The term "aryl" radical means a fused or non-fused monocyclic or polycyclic carbon-based group comprising from 6 to 22 carbon atoms, and in which at least one ring is aromatic; preferentially, the aryl radical is a phenyl, biphenyl, naphthyl, indenyl, anthracenyl or tetrahydronaphthyl.

The term "arylene" radical means a fused or non-fused monocyclic or polycyclic, divalent aromatic carbon-based radical group comprising from 6 to 22 carbon atoms, and in which at least one ring is aromatic, preferably phenylene and more preferentially 1,3-phenylene or 1,4-phenylene.

The term "optionally substituted" attributed to the radical in question means that the said radical may be substituted with one or more radicals chosen from the following radicals: i) hydroxyl, ii) C$_1$-C$_4$ alkoxy, iii) acylamino, iv) amino optionally substituted with one or two identical or different C$_1$-C$_4$ alkyl radicals, the said alkyl radicals possibly forming, with the nitrogen atom that bears them, a 5- to 7-membered heterocycle, optionally comprising another nitrogen or non-nitrogen heteroatom.

According to a preferred embodiment of the invention, the betaine surfactant(s) are chosen from the surfactants of formula (A5) in which n is equal to 1 and G$^-$ denotes an anionic radical chosen from *—C(O)O— and *—S(O)2-O—.

According to an advantageous embodiment of the invention, the betaine surfactant(s) are chosen from the surfactants of formula (A5) in which R$^4$ denotes a linear C$_1$-C$_5$ divalent alkylene radical optionally substituted with a hydroxyl group, such as —CH$_2$—CH$_2$—CH$_2$—, —CH$_2$—CH(OH)—CH$_2$— or —CH$_2$—CH$_2$—.

According to one preferred embodiment of the invention, the betaine surfactant(s) are chosen from the surfactants of formula (A5) in which m is 1 and Z represents an oxygen atom or a group —N(R)— with R as defined previously. More preferentially, when m is 1, then Z represents an oxygen atom.

According to another preferred embodiment of the invention, the betaine surfactant(s) are chosen from the surfactants of formula (A5) in which m is 0.

According to another preferred embodiment of the invention, the betaine surfactant(s) are chosen from the surfactants of formula (A5) in which $R_1$ denotes a group chosen from i) $C_6$-$C_{30}$ alkyl; ii) $C_6$-$C_{30}$ alkenyl; -alkyl($C_6$-$C_{30}$)-amido-($C_1$-$C_4$)alkyl or -alkenyl($C_6$-$C_3$O-amido-($C_1$-$C_4$)alkyl, with amido representing a group —C(O)—N(R)— and R being as defined previously. Particularly, R denotes a hydrogen atom.

More particularly, $R_1$ denotes a linear or branched, preferably linear, $C_6$-$C_{30}$ alkyl radical.

More particularly, the betaine surfactant(s) that may be used in the present invention are chosen from ($C_8$-$C_{20}$) alkylbetaines, sulfobetaines, ($C_8$-$C_{20}$)alkylamido($C_3$-$C_8$) alkylbetaines and ($C_8$-$C_{20}$)alkylamido($C_6$-$C_8$)alkylsulfobetaines, better still from ($C_8$-$C_{20}$)alkylbetaines and ($C_8$-$C_{20}$)alkylamido($C_3$-$C_8$)alkylbetaines and even better still from ($C_8$-$C_{20}$)alkylbetaines.

Even more preferentially, the amphoteric or zwitterionic surfactant according to the invention is cocobetaine.

Preferably, the additional surfactant(s) are chosen from nonionic surfactants and from anionic surfactants. More particularly, the surfactant(s) present in the composition are chosen from nonionic surfactants.

Preferably, the additional surfactant used in the process of the invention in the composition is a monooxyalkylenated or polyoxyalkylenated, particularly monooxyethylenated or polyoxyethylenated, or monooxypropylenated or polyoxypropylenated, nonionic surfactant, or a combination thereof, more particularly monooxyethylenated or polyoxyethylenated.

According to one variant of the invention, the composition and the process for treating (dyeing) keratin fibres use one or more surfactants chosen from monooxyalkylenated or polyoxyalkylenated nonionic surfactants and/or one or more anionic surfactants, in particular of alkyl(ether) sulfate type.

Even more preferably, the additional nonionic surfactants are chosen from polyoxyethylenated sorbitol esters and polyoxyethylenated fatty alcohols, and mixtures thereof.

In the composition of the invention, the amount of the additional surfactant(s) in the composition preferably ranges from 0.1% to 50% by weight and better still from 0.5% to 20% by weight relative to the total weight of the composition.

c) (2,5-Diaminophenyl)Ethanol Oxidation Bases

As indicated above, the dye composition according to the invention comprises c) one or more oxidation bases chosen from (2,5-diaminophenyl)ethanol (or 2-β-hydroxyethyl-para-phenylenediamine) of the following formula, and also acid salts thereof or solvates thereof such as hydrates:

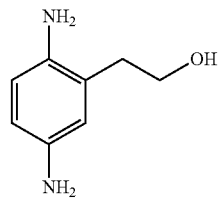 [SMILES: Nc1ccc(N)c(CCO)c1]

The oxidation base(s) chosen from (2,5-diaminophenyl) ethanol and also acid salts thereof or solvates thereof such as hydrates, according to the invention, are advantageously in an amount ranging from 0.0001% to 20% by weight relative to the total weight of the composition, preferably from 0.005% to 10% by weight and more particularly from 0.01% to 10% by weight relative to the total weight of the composition.

The composition according to the invention may also comprise one or more additional oxidation bases other than (2,5-diaminophenyl)ethanol, acid salts thereof or solvates thereof such as hydrates.

According to one particular embodiment of the invention, the additional base(s) are chosen from heterocyclic bases and benzene bases, and the addition salts thereof.

The benzene oxidation bases according to the invention are particularly chosen from para-phenylenediamines, bis (phenyl)alkylenediamines, para-aminophenols and ortho-aminophenols, and the addition salts thereof.

Among the para-phenylenediamines that may be mentioned, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis((3-hydroxyethyl)-para-phenylenediamine, 4-N,N-bis(β-hydroxyethyl)amino-2-methylaniline, 4-N,N-bis(β-hydroxyethyl)amino-2-chloroaniline, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine or PPD, para-tolylenediamine or PTD, 2-isopropyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines that may be mentioned, for example, are N,N'-bis(β-hydroxyethyl)-N, N'-bis(4'-aminophenyl)-1,3-diaminopropanol, N,N'-bis-(β- hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

The heterocyclic bases according to the invention are more particularly chosen from pyridine derivatives, pyrimidine derivatives and pyrazole derivatives, and the addition salts thereof.

Among the pyridine derivatives that may be mentioned are the compounds described, for example, in patents GB 1 026 978 and
GB 1 153 196, for instance 2,5-diaminopyridine, 2-(4-methoxyphenyl)amino-3-aminopyridine and 3,4-diaminopyridine, and the addition salts thereof.

Other pyridine oxidation bases that are useful in the dyeing process according to the invention are the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol and 3-aminopyrazolo[1,5-a]pyridin-7-ol, and the addition salts thereof.

Among the pyrimidine derivatives that may be mentioned are the compounds described, for example, in patents DE 2359399, JP 63-169571, JP 05-163124 and EP 0 770 375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and addition salts thereof, and tautomeric forms thereof, when a tautomeric equilibrium exists.

Among the pyrazole derivatives that may be mentioned are the compounds described in the patents DE 3843892, DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl) pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-amino ethyl) amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof. Use may also be made of 4,5-diamino-1-(β-methoxyethyl)pyrazole.

Use will preferably be made of a 4,5-diaminopyrazole and more preferably still of 4,5-diamino-1-(β-hydroxyethyl) pyrazole and/or a salt thereof.

Mention may also be made, as pyrazole derivatives, of diamino-N,N-dihydropyrazolopyrazolones and in particular those described in application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one or 2,3-diamino-6-hydroxy-6,7-dihydro-1H,5H-pyrazolo[1,2-a]pyrazol-1-one.

Use will preferably be made of 2,3-diamino-6,7-dihydro-1H,5H-pyrazolo[1,2-a]pyrazol-1-one and/or a salt thereof.

Heterocyclic bases that will preferentially be used include 4,5-diamino-1-(β-hydroxyethyl)pyrazole and/or 2,3-diamino-6,7-dihydro-1H,5H-pyrazolo[1,2-a]pyrazol-1-one and/or a salt thereof.

The additional oxidation base(s) according to the invention each advantageously represent from 0.0001% to 10% by weight relative to the total weight of the composition, and preferably from 0.005% to 5% by weight relative to the total weight of the composition.

d) Additional Couplers

The composition of the invention may comprise one or more couplers.

According to a preferred embodiment, the dye composition and the dyeing process use one or more couplers. Mention may in particular be made, among these couplers, of meta-phenylenediamines, meta-aminophenols, meta-diphenols, naphthalene-based couplers and heterocyclic couplers, and also addition salts thereof.

Mention may be made, for example, of 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1- methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

The coupler(s) each advantageously represent from 0.0001% to 10% by weight, relative to the total weight of the composition, and preferably from 0.005% to 5% by weight, relative to the total weight of the composition of the invention.

In general, the addition salts of the oxidation bases and couplers which can be used in the context of the invention are selected in particular from the addition salts with an acid, such as the hydrochlorides, hydrobromides, sulfates, citrates, succinates, tartrates, lactates, tosylates, benzenesulfonates, phosphates and acetates.

In one variant of the invention, the composition does not contain any para-phenylenediamine (PPD) and/or the process for treating keratin fibres does not use PPD. According to another advantageous embodiment, the composition and/or the process for treating keratin fibres do not use chlorinated bases or halogenated couplers, in particular chlorinated bases or couplers such as those chosen from 2-amino-6-chloro-4-nitrophenol, 2,6-dichloro-4-aminophenol, 2-chloro-6-ethylamino-4-nitrophenol, 3-amino-5-chloroaniline, 2-chloro-4-aminophenol and 2-chloro-6-methyl-3-aminophenol. According to another particular embodiment, the composition and/or the process for treating keratin fibres do not use 3-(2,4-diaminophenoxy)-1-propanol couplers.

Additional Dyes

The composition of the invention may also comprise one or more direct dyes. The latter are more particularly chosen from ionic or nonionic species, preferably cationic or nonionic species. These direct dyes may be synthetic or of natural origin.

Examples of suitable direct dyes that may be mentioned include the following direct dyes: azo dyes; methine dyes; carbonyl dyes; azine dyes; nitro(hetero)aryl dyes; tri(hetero)arylmethane dyes; porphyrin dyes; phthalocyanin dyes, and natural direct dyes, alone or as mixtures.

More particularly, the azo dyes comprise an —N=N— function in which the two nitrogen atoms are not simultaneously engaged in a ring. However, it is not excluded for one of the two nitrogen atoms of the sequence —N=N— to be engaged in a ring.

The dyes of the methine family are more particularly compounds comprising at least one sequence chosen from >C=C< and —N=C< in which the two atoms are not simultaneously engaged in a ring. However, it is pointed out that one of the nitrogen or carbon atoms of the sequences may be engaged in a ring. More particularly, the dyes of this family are derived from compounds of the type such as methines, azomethines, monoarylmethanes and diarylmethanes, indoamines, indoamines (or diphenylamines), indophenols, indoanilines, carbocyanins, azacarbocyanins and isomers thereof, diazacarbocyanins and isomers thereof, tetraazacarbocyanins and hemicyanins.

As regards the dyes of the carbonyl family, examples that may be mentioned include dyes chosen from acridone, benzoquinone, anthraquinone, naphthoquinone, benzanthrone, anthranthrone, pyranthrone, pyrazolanthrone, pyrimidinoanthrone, flavanthrone, idanthrone, flavone, (iso) violanthrone, isoindolinone, benzimidazolone, isoquinolinone, anthrapyridone, pyrazoloquinazolone, perinone, quinacridone, quinophthalone, indigo id, thio indigo, naphthalimide, anthrapyrimidine, diketopyrrolopyrrole and coumarin.

As regards the dyes of the cyclic azine family, mention may be made especially of azine, xanthene, thioxanthene, fluorindine, acridine, (di)oxazine, (di)thiazine and pyronin.

The nitro(hetero)aromatic dyes are more particularly nitrobenzene or nitropyridine direct dyes.

As regards the dyes of porphyrin or phthalocyanin type, use may be made of cationic or non-cationic compounds optionally comprising one or more metals or metal ions, for instance alkali metals, alkaline-earth metals, zinc and silicon.

Examples of particularly suitable direct dyes that may be mentioned include nitrobenzene dyes; azo direct dyes; azomethine direct dyes; methine direct dyes; azacarbocyanin direct dyes, for instance tetraazacarbocyanins (tetraazapentamethines); quinone and in particular anthraquinone, naphthoquinone or benzoquinone direct dyes; azine direct dyes; xanthene direct dyes; triarylmethane direct dyes; indoamine direct dyes; indigoid direct dyes; phthalocyanin direct dyes, porphyrin direct dyes and natural direct dyes, alone or as mixtures.

Among the natural dyes that may be used according to the invention, mention may be made of lawsone, juglone, alizarin, purpurin, carminic acid, kermesic acid, purpurogallin, protocatechaldehyde, indigo, isatin, curcumin, spinulosin, apigenidin, haematin, haematoxylin, brasilin, brasilein and orceins. Use may also be made of extracts or decoctions comprising these natural dyes and in particular henna-based poultices or extracts.

When they are present, the direct dye(s) more particularly represent from 0.0001% to 10% by weight and preferably from 0.005% to 5% by weight of the total weight of the composition.

e) Additional Basifying Agents:

The composition of the invention may also comprise e) one or more basifying agents.

According to one embodiment of the invention, the composition and the process for treating keratin fibres use one or more basifying agents. The basifying agent(s) may be inorganic or organic or hybrid.

The inorganic basifying agent(s) are preferably chosen from aqueous ammonia, alkali metal carbonates or bicarbonates such as sodium carbonate, potassium carbonate, sodium bicarbonate or potassium bicarbonate, sodium hydroxide or potassium hydroxide, or mixtures thereof.

The organic basifying agent(s) are preferably chosen from organic amines with a $pK_b$ at 25° C. of less than 12, preferably less than 10 and even more advantageously less than 6. It should be noted that it is the $pK_b$ corresponding to the function of highest basicity. In addition, the organic amines do not comprise an alkyl or alkenyl fatty chain comprising more than ten carbon atoms.

The organic basifying agent(s) are chosen, for example, from alkanolamines, oxyethylenated and/or oxypropylenated ethylenediamines, amino acids and the compounds of formula (VII) below:

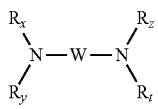 (VII)

in which formula (VII) W is a divalent $C_1$-$C_6$ alkylene radical optionally substituted with one or more hydroxyl groups or a $C_1$-$C_6$ alkyl radical, and/or optionally interrupted with one or more heteroatoms such as O, or $NR_u$; $R_x$, $R_y$, $R_z$, $R_t$ and $R_u$, which may be identical or different, represent a hydrogen atom or a $C_1$-$C_6$ alkyl, $C_1$-$C_6$ hydroxyalkyl or $C_1$-$C_6$ aminoalkyl radical.

Examples of amines of formula (VII) that may be mentioned include 1,3-diaminopropane, 1,3-diamino-2-propanol, spermine and spermidine.

The term "alkanolamine" means an organic amine comprising a primary, secondary or tertiary amine function, and one or more linear or branched $C_1$-$C_8$ alkyl groups bearing one or more hydroxyl radicals.

The organic amines chosen from alkanolamines such as monoalkanolamines, dialkanolamines or trialkanolamines comprising one to three identical or different $C_1$-$C_4$ hydroxyalkyl radicals are in particular suitable for performing the invention.

Among the compounds of this type, mention may be made of monoethanolamine (MEA), diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

More particularly, the amino acids that may be used are of natural or synthetic origin, in their L, D or racemic form, and comprise at least one acid function chosen more particularly from carboxylic acid, sulfonic acid, phosphonic acid or phosphoric acid functions. The amino acids can be in the neutral or ionic form.

Mention may in particular be made, as amino acids which can be used in the present invention, of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Advantageously, the amino acids are basic amino acids comprising an additional amine function optionally included in a ring or in a ureido function.

Such basic amino acids are preferably chosen from those corresponding to formula (VIII) below:

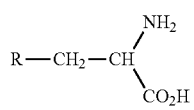 (VIII)

in which formula (VIII) R represents a group chosen from:

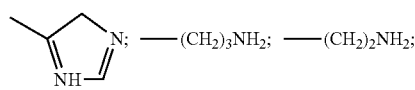

-continued

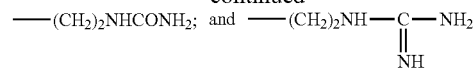

The compounds corresponding to formula (VIII) are histidine, lysine, arginine, ornithine and citrulline.

The organic amine may also be chosen from organic amines of heterocyclic type. Mention may in particular be made, in addition to histidine, already mentioned in the amino acids, of pyridine, piperidine, imidazole, triazole, tetrazole or benzimidazole.

The organic amine can also be chosen from amino acid dipeptides. As amino acid dipeptides that may be used in the present invention, mention may be made especially of carnosine, anserine and balenine.

The organic amine may also be chosen from compounds comprising a guanidine function. As amines of this type that can be used in the present invention, besides arginine, which has already been mentioned as an amino acid, mention may be made especially of creatine, creatinine, 1,1-dimethylguanidine, 1,1-diethylguanidine, glycocyamine, metformin, agmatine, N-amidino alanine, 3-guanidinopropionic acid, 4-guanidinobutyric acid and 2-([amino(imino)methyl]amino)ethane-1-sulfonic acid.

Hybrid compounds that may be mentioned include the salts of the amines mentioned previously with acids such as carbonic acid or hydrochloric acid.

Use may in particular be made of guanidine carbonate or monoethanolamine hydrochloride.

Preferably, the basifying agent(s) present in the composition of the invention are chosen from alkanolamines, amino acids in neutral or ionic form, in particular basic amino acids, and preferably corresponding to those having the formula (III).

Even more preferentially, the basifying agent(s) are chosen from monoethanolamine (MEA) and basic amino acids in neutral or ionic form.

Advantageously, the composition according to the invention has a content of basifying agent(s) ranging from 0.01% to 30% by weight and preferably from 0.1% to 20% by weight relative to the weight of the composition.

According to a first particular embodiment, the composition or the process according to the invention does not contain/use any aqueous ammonia, or a salt thereof, as basifying agent.

If, however, according to another particular embodiment, the composition or the process did use any, its content would advantageously not exceed 0.03% by weight (expressed as $NH_3$) and would preferably not exceed 0.01% by weight relative to the weight of the composition of the invention. Preferably, if the composition comprises aqueous ammonia, or a salt thereof, then the amount of basifying agent(s) other than the aqueous ammonia is greater than that of the aqueous ammonia (expressed as $NH_3$).

f) Chemical Oxidizing Agent

The composition of the invention comprises f) one or more chemical oxidizing agents. The term "chemical oxidizing agent" means an oxidizing agent other than atmospheric oxygen.

The composition of the invention preferentially contains one or more chemical oxidizing agents.

More particularly, the chemical oxidizing agent(s) are chosen from hydrogen peroxide, urea peroxide, alkali metal bromates, peroxygenated salts, for instance persulfates or perborates, peracids and precursors thereof and alkali metal or alkaline-earth metal percarbonates.

This oxidizing agent is advantageously constituted of hydrogen peroxide.

The concentration of chemical oxidizing agents may range more particularly from 0.1% to 50% by weight, even more preferentially from 0.5% to 20% by weight and better still from 1% to 15% by weight relative to the weight of the composition.

Preferably, the composition of the invention does not contain any peroxygenated salts.

Solvent

The composition according to the invention can also comprise one or more organic solvents.

Examples of organic solvents that may be mentioned include linear or branched $C_2$-$C_4$ alkanols, such as ethanol and isopropanol; glycerol; polyols and polyol ethers, for instance 2-butoxyethanol, propylene glycol, dipropylene glycol, propylene glycol monomethyl ether, diethylene glycol monomethyl ether and monoethyl ether, and also aromatic alcohols or ethers, for instance benzyl alcohol or phenoxyethanol, and mixtures thereof.

The solvent(s), if they are present, represent a content usually ranging from 1% to 40% by weight and preferably from 5% to 30% by weight relative to the weight of the composition.

Other Additives

The composition according to the invention may also contain various adjuvants conventionally used in hair dye compositions, such as anionic, cationic, nonionic, amphoteric or zwitterionic polymers or mixtures thereof; inorganic thickeners, and in particular fillers such as clays or talc; organic thickeners with, in particular, anionic, cationic, nonionic and amphoteric polymeric associative thickeners; antioxidants; penetrants; sequestrants; fragrances; dispersants; film-forming agents; ceramides; preserving agents; opacifiers.

The above adjuvants are generally present in an amount for each of them of between 0.01% and 20% by weight relative to the weight of the composition.

The composition may especially comprise one or more inorganic thickeners chosen from organophilic clays and fumed silicas, or their mixtures.

The organophilic clay may be chosen from montmorillonite, bentonite, hectorite, attapulgite and sepiolite, and mixtures thereof. The clay is preferably a bentonite or a hectorite.

These clays may be modified with a chemical compound chosen from quaternary amines, tertiary amines, amine acetates, imidazolines, amine soaps, fatty sulfates, alkylarylsulfonates and amine oxides, and mixtures thereof.

Mention may be made, as organophilic clays, of quaternium-18 bentonites, such as those sold under the names Bentone 3, Bentone 38 and Bentone 38V by Rheox, Tixogel VP by United Catalyst and Claytone 34, Claytone 40 and Claytone XL by Southern Clay; stearalkonium bentonites, such as those sold under the names Bentone 27 by Rheox, Tixogel LG by United Catalyst and Claytone AF and Claytone APA by Southern Clay; and quaternium-18/benzalkonium bentonites, such as those sold under the names Claytone HT and Claytone PS by Southern Clay.

The fumed silicas can be obtained by high-temperature hydrolysis of a volatile silicon compound in an oxyhydrogen flame, producing a finely divided silica. This process makes it possible in particular to obtain hydrophilic silicas which contain a large number of silanol groups at their surface. Such hydrophilic silicas are sold, for example, under the names Aerosil 130®, Aerosil 200®, Aerosil 255®, Aerosil 300® and Aerosil 380® by Degussa and Cab-O-Sil HS-5®, Cab-O-Sil EH-5®, Cab-O-Sil LM-130®, Cab-O-Sil MS-55® and Cab-O-Sil M-5® by Cabot.

It is possible to chemically modify the surface of the silica by chemical reaction for the purpose of reducing the number of silanol groups. It is possible in particular to replace silanol groups with hydrophobic groups: a hydrophobic silica is then obtained.

The hydrophobic groups can be:
trimethylsiloxyl groups, which are obtained in particular by treating fumed silica in the presence of hexamethyldisilazane. Silicas thus treated are known as "Silica silylate" according to the CTFA (6th Edition, 1995). They are sold, for example, under the references Aerosil R812® by the company Degussa and Cab-O-Sil TS-530® by the company Cabot.
dimethylsilyloxyl or polydimethylsiloxane groups, which are obtained in particular by treating fumed silica in the presence of polydimethylsiloxane or dimethyldichlorosilane. Silicas thus treated are known as "Silica dimethyl silylate" according to the CTFA (6th Edition, 1995). They are sold, for example, under the references Aerosil R972® and Aerosil R974® by the company Degussa and Cab-O-Sil TS-610® and Cab-O-Sil TS-720® by the company Cabot.

The fumed silica preferably has a particle size that may be nanometric to micrometric, for example ranging from about 5 to 200 nm.

Preferably, the composition comprises a hectorite, an organomodified bentonite or an optionally modified fumed silica.

When it is present, the inorganic thickener represents from 1% to 30% by weight relative to the weight of the composition.

The composition may also comprise one or more organic thickeners.

These thickeners may be chosen from fatty acid amides (coconut acid diethanolamide or monoethanolamide, oxyethylenated alkyl ether carboxylic acid monoethanolamide), polymeric thickeners, such as cellulose thickeners (hydroxyethylcellulose, hydroxypropylcellulose, carboxymethylcellulose), guar gum and its derivatives (hydroxypropyl guar), gums of microbial origin (xanthan gum, scleroglucan gum), crosslinked homopolymers of acrylic acid or of acrylamidopropanesulfonic acid and associative polymers (polymers comprising hydrophilic regions and hydrophobic regions having a fatty chain (alkyl or alkenyl chain comprising at least 10 carbon atoms) which are capable, in an aqueous medium, of reversibly associating with one another or with other molecules).

According to a specific embodiment, the organic thickener is chosen from cellulose-based thickeners (hydroxyethylcellulose, hydroxypropylcellulose, carboxymethylcellulose), guar gum and derivatives thereof (hydroxypropyl guar), gums of microbial origin (xanthan gum, scleroglucan gum) and crosslinked homopolymers of acrylic acid or of acrylamidopropanesulfonic acid, and preferably from cellulose-based thickeners with in particular hydroxyethylcellulose.

The content of organic thickener(s), if they are present, usually ranges from 0.01% to 20% by weight and preferably from 0.1% to 5% by weight, relative to the weight of the composition.

The composition of the invention may be in various forms, for instance a solution, an emulsion (milk or cream) or a gel, preferably in the form of an emulsion and particularly of a direct emulsion.

Preferably, the dye composition comprises one or more non-silicone liquid fatty substances, one or more alkyl(poly) glucoside nonionic surfactants and/or one or more oxyethylenated $C_8$ to $C_{30}$ fatty acid esters of sorbitan, and/or one or more (poly)alkoxylated fatty alcohol(s), and/or one or more (poly)glycerolated alcohol(s); one or more oxidation bases chosen from (2,5-diaminophenyl)ethanol and also acid salts thereof or solvates thereof such as hydrates, one or more couplers and one or more chemical oxidizing agents.

Preferably, the composition for dyeing keratin fibres, in particular human keratin fibre such as the hair comprises:

a) one or fatty substances, which are preferably non-silicone liquids, b) one or more alkyl(poly)glucoside non ionic surfactants or one or more oxyethylenated $C_8$ to $C_{30}$ fatty acid ester(s) of sorbitan or one or more (poly)alkoxylated alcohols or one more (poly)glycerolated alcohols, c) one or more oxidation base(s) chosen from (2,5-diaminophenyl)ethanol and also acid salts thereof or solvates thereof such as hydrates;

d) optionally one or more coupler(s);

e) optionally one or more basifying agent(s);

f) one or more chemical oxidizing agent(s); and the fatty substance content representing in total at least 20% by weight relative to the total weight of the composition.

Processes of the Invention

The dyeing process according to the invention consists in applying the composition comprising ingredients a) to f) as defined previously to wet or dry keratin fibres. The composition is left in place on the fibres for a time generally of from 1 minute to 1 hour and preferably from 5 minutes to 30 minutes.

The temperature during the dyeing process is conventionally between room temperature (between 15° C. and 25° C.) and 80° C. and preferably between room temperature and 60° C.

After the treatment, the human keratin fibres are optionally rinsed with water, optionally washed with a shampoo and then rinsed with water, before being dried or left to dry.

The composition according to the invention is generally prepared by mixing at least two compositions, preferably two or three compositions.

In a first variant of the invention, the composition according to the invention comprising the ingredients a) to f) as defined previously results from the mixing of two compositions:

a composition (A) comprising c) one or more oxidation bases chosen from (2,5-diaminophenyl)ethanol and also acid salts thereof or solvates thereof such as hydrates; d) optionally one or more couplers as defined previously; e) one or more basifying agents as defined previously; and a composition (B) comprising f) one or more chemical oxidizing agents as defined previously, it being understood that:

at least one of the compositions (A) or (B) comprises a) one or more fatty substances, which are preferably non-silicone liquids as defined previously, and b) one or more alkyl(poly)glucoside nonionic surfactants, and/or one or more oxyethylenated $C_8$ to $C_{30}$ fatty acid esters of sorbitan, and/or one or more (poly)alkoxylated fatty alcohol(s) and/or one or more (poly)glycerolated alcohol(s); as defined previously, such that the fatty substance content of the composition according to the invention resulting from the mixing of compositions (A)+(B) is at least 20% by weight, preferably at least 25% by weight, more preferably at least 30% by weight, better still at least 40% by weight and even better still at least 50% by weight, relative to the total weight of the mixture of (A)+(B).

Preferentially, at least one of the compositions (A) or (B) is aqueous.

Even more preferentially, both the compositions (A) and (B) are aqueous.

The term "aqueous composition" means a composition comprising at least 5% by weight of water. Preferably, an aqueous composition comprises more than 10% by weight of water and more advantageously still more than 20% by weight of water.

Preferably, composition (A) is aqueous.

In this variant, composition (A) comprises at least 50% by weight of fatty substances and even more preferentially at least 50% by weight of non-silicone fatty substances that are liquid at room temperature (25° C.).

Preferably, composition (A) is a direct or inverse emulsion and preferably a direct (O/W) emulsion.

In this variant, compositions (A) and (B) are preferably mixed in an (A)/(B) weight ratio ranging from 0.2 to 10 and better still from 0.5 to 2.

In accordance with this first variant, the dyeing process therefore consists in applying to the keratin fibres the dye composition resulting from the mixing of the compositions (A) and (B) mentioned above.

According to one particular embodiment of this first variant, the alkyl(poly)glucoside nonionic surfactant(s) and/or the oxyethylenated $C_8$ to $C_{30}$ fatty acid ester(s) of sorbitan and/or the (poly)alkoxylated fatty alcohol(s) and/or the (poly)glycerolated alcohol(s) are included in composition (A).

According to another particular embodiment of this first variant, the alkyl(poly)glucoside nonionic surfactant(s) and/or the oxyethylenated $C_8$ to $C_{30}$ fatty acid ester(s) of sorbitan and/or the (poly)alkoxylated fatty alcohol(s) and/or the (poly)glycerolated alcohol(s) are included in composition (B).

In a second variant of the invention, the composition according to the invention comprising ingredients a) to f) as defined previously results from the mixing of three compositions, the three compositions being aqueous or at least one of them being anhydrous.

More particularly, for the purposes of the invention, the expression "anhydrous cosmetic composition" means a cosmetic composition with a water content of less than 5% by weight, preferably less than 2% by weight and more preferably still less than 1% by weight relative to the weight of the said composition. It should be noted that the water present in the composition is more particularly "bound water", such as the water of crystallization of the salts or traces of water absorbed by the raw materials used in the preparation of the compositions according to the invention.

In this second variant, use will preferably be made of two aqueous compositions (B') and (C') and an anhydrous composition (A').

The anhydrous composition (A') then preferably comprises a) one or more fatty substances as defined previously and more preferentially one or more liquid fatty substances.

Composition (B') then preferably comprises c) one or more oxidation bases chosen from (2,5-diaminophenyl)ethanol and also acid salts thereof or solvates thereof such as hydrates and d) optionally one or more couplers as defined previously.

Composition (C') then preferably comprises f) one or more chemical oxidizing agents as defined previously.

The basifying agent(s) e) as defined previously are included in compositions (A') and/or (B') and preferably solely in composition (B').

The alkyl(poly)glucoside nonionic surfactant(s) and/or the oxyethylenated $C_8$ to $C_{30}$ fatty acid ester(s) of sorbitan and/or the (poly)alkoxylated fatty alcohol(s) and/or the (poly)glycerolated alcohol(s) as defined previously are included in at least one of the compositions (A'), (B') or (C'), these three compositions being such that the fatty substance content of the composition according to the invention resulting from the mixing of the three compositions (A')+(B')+(C') is greater than or equal to 20% by weight relative to the total weight of the mixture of the three compositions (A')+(B')+(C'), and more preferentially greater than or equal to 25% by weight, more preferably greater than or equal to 30% by weight, better still greater than or equal to 40% by weight and even better still greater than or equal to 50% by weight, relative to the total weight of the mixture of (A)+(B).

In this variant, the compositions (A'), (B') and (C') are preferably mixed in an (A')+(B')/(C') weight ratio ranging from 0.2 to 10 and better still from 0.5 to 2 and in an (A')/(B') weight ratio ranging from 0.5 to 10 and better still from 1 to 5.

In accordance with this second variant, the dyeing process therefore consists in applying to the keratin fibres the dye composition resulting from the mixing of the compositions (A'), (B') and (C') mentioned above.

Dyeing Device

Finally, the invention relates to a first multi-compartment device comprising a first compartment containing composition (A) as described above and at least a second compartment containing composition (B) as described above, the compositions of the compartments being intended to be mixed before application to give the formulation after mixing according to the invention, provided that the amount of fatty substance in this formulation represents at least 20% by weight, preferably at least 25% by weight, more preferably at least 30% by weight, better still at least 40% by weight and even better still at least 50% by weight, relative to the total weight of the formulation resulting from the mixing of (A)+(B).

The invention also relates to a second multi-compartment device comprising a first compartment containing composition (A') as described above and a second compartment containing a cosmetic composition (B') as described above and at least a third compartment comprising composition (C') as described above, the compositions of the compartments being intended to be mixed before application to give the formulation after mixing according to the invention, provided that the amount of fatty substance in this formulation represents at least 20% by weight, preferably at least 25% by weight, more preferably at least 30% by weight, better still at least 40% by weight and even better still at least 50% by weight relative to the weight of the formulation resulting from the mixing of (A')+(B')+(C').

The examples that follow serve to illustrate the invention without, however, being limiting in nature.

The evaluation of the coloration can be done visually or read on a spectrocolorimeter (such as Minolta CM3600d, illuminant D65, angle 10°, SCI values) for the L*, a*, b* colorimetric measurements. In this L*, a*, b* system, L* represents the intensity of the color, a* indicates the green/red color axis and b* indicates the blue/yellow color axis. The lower the value of L, the darker or more intense the color. The higher the value of a*, the redder the shade; the higher the value of b*, the yellower the shade. The variation in coloring between the colored locks of natural white hair (NW) which is untreated (control) and after treatment or coloration are defined by ΔE*, corresponding to the colour uptake on keratin fibers, according to the following equation:

$$\Delta E^* = \sqrt{(L^* - L_o^*)^2 + (a^* - a_o^*)^2 + (b^* - b_o^*)^2}$$

In this equation, L*, a* and b* represent the values measured after dyeing the natural hair comprising 90% of white hairs and $L_o^*$, $a_o^*$ and $b_o^*$ represent the values measured for the untreated natural hair comprising 90% of white hairs.

The greater the value of ΔE, the greater the difference in color between the control locks and the dyed locks and the greater colour uptake is.

On the other hand for evaluating the selectivity of the color between the root and tip of the keratin fiber, measurement can be done on permed or sensibilised white hair (PW) and natural white hair, wherein the variation in coloring between the colored locks PW and the colored natural white hair are defined by ΔE*, corresponding to the selectivity of the colour, is calculated according to the following equation:

$$\Delta E^* = \sqrt{(L^* - L_o^*)^2 + (a^* - a_o^*)^2 + (b^* - b_o^*)^2}$$

In this equation, L*, a* and b* represent the values measured after dyeing the natural hair comprising 90% of white hairs and $L_o^*$, $a_o^*$ and $b_o^*$ represent the values measured after dyeing the permed or sensibilised hair. The lowest ΔE*, the best homogeneity of the hair color.

If the light fastness is investigated, ΔE* is also calculated for the $L_o^*$, $a_o^*$, $b_o^*$ and L*, a*, b* measured of the locks before and after exposure to the light, respectively.

Chromaticity in the CIE L*, a*, b* colorimetric system is calculated according to the following equation:

$$C^* = \sqrt{a^{*2} + b^{*2}}$$

The greater the value of C*, the greater the chromaticity is.

The examples that follow serve to illustrate the invention without, however, being limiting in nature.

EXAMPLE 1

The following compositions are prepared, in which the amounts are expressed in grams of product in their given state.

1. Dye Compositions a. Dye Composition A1:

| Composition | A1 |
|---|---|
| Liquid petroleum jelly (fatty substance a) | 59.7 |
| Tamanu kernel oil | 0.1 |
| Argan oil | 0.1 |
| Safflower oil | 0.1 |
| 2-(2,5-Diaminophenyl)ethanol sulfate (oxidation base c) | 1.58 |
| 6-hydroxybenzomorpholine (coupler d) | 0.033 |
| 1-β-Hydroxyethyloxy-2,4-diaminobenzene dihydrochloride (coupler d) | 0.02 |
| 1,3-Dihydroxybenzene (resorcinol) (coupler d) | 0.67 |
| 1-Hydroxy-3-aminobenzene (coupler d) | 0.12 |
| Cationic hydroxyethylcellulose (Softcat SL 100 from Amerchol) | 0.2 |

-continued

| Composition | A1 |
|---|---|
| Oxyethylenated (2 OE) stearyl alcohol | 1.13 |
| Oxyethylenated (20 OE) stearyl alcohol | 3.88 |
| C8-C10 Alkyl polyglucoside as an aqueous 60% solution (Oramix CG 110 from SEPPIC) | 4 |
| Sorbitan monolaurate 4 OE | 2.4 |
| Monoethanolamine | 4.39 |
| Sequestrant | 0.2 |
| Reducing agent | 0.45 |
| Antioxidant | 0.25 |
| Deionized water | qs 100 g | b. Dye Composition A2:

| Composition | A2 |
|---|---|
| Liquid petroleum jelly (fatty substance a) | 59.7 |
| Oxyethylenated (40 OE) hydrogenated castor oil (fatty substance a) | 1 |
| Cocoylbetaine at 30% as an aqueous solution | 10 |
| 2-(2,5-Diaminophenyl)ethanol sulfate (oxidation base c) | 1.58 |
| 6-hydroxybenzomorpholine (coupler d) | 0.033 |
| 1-β-Hydroxyethyloxy-2,4-diaminobenzene dihydrochloride (coupler d) | 0.02 |
| 1,3-Dihydroxybenzene (resorcinol) (coupler d) | 0.67 |
| 1-Hydroxy-3-aminobenzene (coupler d) | 0.12 |
| Pure monoethanolamine (basifying agent e) | 5.16 |
| Hydroxyethylcellulose (MW: 1 300 000) | 2.5 |
| Oxyethylenated (2 OE) stearyl alcohol | 0.1 |
| Oxyethylenated (20 OE) stearyl alcohol | 0.1 |
| Sodium lauryl ether sulfate (2.2 OE) at 70% as an aqueous solution | 2.5 |
| Sequestrant | 2 |
| Reducing agent | 0.5 |
| Antioxidant | 0.5 |
| Deionized water | qs 100 |

2. Oxidizing Compositions:
a. Oxidizing Composition B1

| Composition | B1 |
|---|---|
| 50% Aqueous hydrogen peroxide solution (200-volumes aqueous hydrogen peroxide solution) (chemical oxidizing agent f) | 6 |
| Etidronic acid, tetrasodium salt as an aqueous 30% solution | 0.2 |
| Tetrasodium pyrophosphate decahydrate | 0.04 |
| Sodium salicylate | 0.035 |
| Dimethyldiallylammonium chloride/acrylic acid copolymer (80/20) as an aqueous 40.5% solution (Merquat 280 from Nalco) | 0.74 |
| Glycerol | 4 |
| (50/50 C$_8$/C$_{10}$) Alkyl polyglucoside as an aqueous 60% solution (Oramix CG 110 from SEPPIC) | 3 |
| Deionized water | qs 100 g | b. Oxidizing Composition B2

| Composition | B2 |
|---|---|
| 50% Aqueous hydrogen peroxide solution (200-volumes aqueous hydrogen peroxide solution) (chemical oxidizing agent f) | 6 |
| Etidronic acid, tetrasodium salt as an aqueous 30% solution | 0.2 |
| Tetrasodium pyrophosphate decahydrate | 0.04 |
| Sodium salicylate | 0.035 |
| Dimethyldiallylammonium chloride/acrylic acid copolymer (80/20) as an aqueous 40.5% solution (Merquat 280 from Nalco) | 0.74 |
| Glycerol | 4 |
| Deionized water | qs 100 g |

3. Procedure

The dye compositions A1 and A2 are mixed, respectively, with the oxidizing compositions B2 and B1, at a rate of one part of dye composition per one part of oxidizing composition.

The mixtures A1+B2 and A2+B1 are then applied to locks of hair comprising 90% white hairs, at a rate of 10 grams of mixture per one gram of lock.

After a leave-on time of 35 minutes at 27° C., the hair is rinsed with clear water and a conditioning shampoo is then applied to the hair.

After drying, a light chestnut-brown shade of good strength and coverage is obtained on the hair.

EXAMPLE 2

The following compositions are prepared, in which the amounts are expressed in grams of product in their given state.

Dye Composition A3:

| Composition | A3 |
|---|---|
| Liquid petroleum jelly (fatty substance a) | 59.7 |
| Safflower oil (6/12/78 palmitic-oleic-linoleic acid triglycerides) (fatty substance a) | 0.1 |
| Tamanu kernel oil (fatty substance a) | 0.1 |
| Argan oil (fatty substance a) | 0.1 |
| Oxyethylenated sorbitan monolaurate (4 OE) (surfactant b) | 2.4 |
| 2-(2,5-Diaminophenyl)ethanol sulfate (oxidation base c) | 1.58 |
| 6-Hydroxybenzomorpholine (coupler d) | 0.033 |
| 1-β-Hydroxyethyloxy-2,4-diaminobenzene dihydrochloride (coupler d) | 0.02 |
| 1,3-Dihydroxybenzene (resorcinol) (coupler d) | 0.67 |
| 1-Hydroxy-3-aminobenzene (coupler d) | 0.12 |
| Pure monoethanolamine (basifying agent e) | 4.39 |
| Cationic hydroxyethylcellulose (Softcat SL 100 from Amerchol) | 0.2 |
| Ethylenediaminetetraacetic acid | 0.2 |
| Oxyethylenated (2 OE) stearyl alcohol | 1.13 |
| Oxyethylenated (20 OE) stearyl alcohol | 3.88 |
| (50/50 C$_8$/C$_{10}$) Alkyl polyglucoside as an aqueous 60% solution (Oramix CG 110 from SEPPIC) | 4 |
| Reducing agent | 0.45 |
| Antioxidant | 0.25 |
| Fragrance | 0.72 |
| Deionized water | qs 100 |

Dye Composition A4

| Composition | A4 |
|---|---|
| Liquid petroleum jelly (fatty substance a) | 50 |
| Oxyethylenated sorbitan monolaurate (4 OE) (surfactant b) | 5 |
| 2-(2,5-Diaminophenyl)ethanol sulfate (oxidation base c) | 1.58 |
| 6-Hydroxybenzomorpholine (coupler d) | 0.033 |
| 1-β-Hydroxyethyloxy-2,4-diaminobenzene dihydrochloride (coupler d) | 0.02 |

-continued

| Composition | A4 |
|---|---|
| 1,3-Dihydroxybenzene (resorcinol) (coupler d) | 0.67 |
| 1-Hydroxy-3-aminobenzene (coupler d) | 0.12 |
| Pure monoethanolamine (basifying agent e) | 5.4 |
| Cetylstearyl alcohol (50/50 $C_{16}/C_{18}$) | 2.5 |
| Carboxyvinyl polymer (Carbopol 980 from Lubrizol) | 0.4 |
| Sodium cetostearyl sulfate (50/50 $C_{16}/C_{18}$) (Lanette E from Cognis) | 2 |
| Oxyethylenated (20 OE) stearyl alcohol | 2 |
| Sequestrant | 0.2 |
| Reducing agent | 0.4 |
| Antioxidant | 0.3 |
| Deionized water | qs 100 |

Oxidizing Composition B3

| Composition | B3 |
|---|---|
| 50% Aqueous hydrogen peroxide solution (200-volumes aqueous hydrogen peroxide solution) (chemical oxidizing agent f) | 12 |
| Disodium tin hexahydroxide | 0.04 |
| Tetrasodium pyrophosphate decahydrate | 0.03 |
| Liquid petroleum jelly | 20 |
| Poly[(dimethylimino)-1,3-propanediyl(dimethylimino)-1,6-hexanediyl dichloride] as an aqueous 60% solution (Mexomer PO from Chimex) | 0.25 |
| Polydimethyldiallylammonium chloride at 40% in water (Merquat 100 from Nalco) | 0.5 |
| Glycerol | 0.5 |
| Cetearyl alcohol (30/70 $C_{16}/C_{18}$) | 6 |
| Oxyethylenated (20 OE) stearyl alcohol | 5 |
| Protected oxyethylenated (4 OE) rapeseed acid amide | 1.3 |
| Vitamin E: DL-α-Tocopherol | 0.1 |
| Sequestrant | 0.15 |
| Deionized water | qs 100 |

3. Procedure

The dye compositions A3 and A4 are mixed with the oxidizing composition B3, at a rate of one part of dye composition per one part of oxidizing composition.

The mixtures A3+B3 and A4+B3 are then applied to locks of hair comprising 90% white hairs, at a rate of 10 grams of mixture per one gram of lock.

After a leave-on time of 35 minutes at 27° C., the hair is rinsed with clear water and a conditioning shampoo is then applied to the hair.

After drying, a light chestnut-brown shade of good strength and coverage is obtained on the hair.

EXAMPLE 3

The following compositions are prepared, in which the amounts are expressed in grams of product in their given state.

Dye compositions A5 to A11:

| Ingredients | A5 | A6 | A7 | A8 |
|---|---|---|---|---|
| Liquid petroleum jelly (fatty substance a) | 60 | 60 | 60 | 59.7 |
| Non-stabilized safflower oil (6/12/78 palmitic-oleic-linoleic acid triglycerides) (fatty substance a) | — | — | — | 0.1 |
| Refined tamanu kernel oil (fatty substance a) | — | — | — | 0.1 |
| Virgin argan oil (fatty substance a) | — | — | — | 0.1 |
| Oxyethylenated (40 OE) hydrogenated castor oil (fatty substance a) | — | — | 1 | — |
| Mixture of linear $C_{18}$ to $C_{24}$ alcohols (7/58/30/6 $C_{18}/C_{20}/C_{22}/C_{24}$) Alcohol content > 95% (fatty substance a) | 4.6 | 4.6 | — | — |
| 2-(2,5-Diaminophenyl)ethanol sulfate (oxidation base c) | 1.58 | 1.58 | 1.58 | 1.58 |
| 6-Hydroxybenzomorpholine (coupler d) | 0.033 | 0.033 | 0.033 | 0.033 |
| 1-β-Hydroxyethyloxy-2,4-diaminobenzene dihydrochloride (coupler d) | 0.02 | 0.02 | 0.02 | 0.02 |
| 1,3-Dihydroxybenzene (resorcinol) (coupler d) | 0.67 | 0.67 | 0.67 | 0.67 |
| 1-Hydroxy-3-aminobenzene (coupler d) | 0.12 | 0.12 | 0.12 | 0.12 |
| Pure monoethanolamine MEA (basifying agent e) | 4.28 | 4.78 | 5.16 | 4.39 |
| Carboxyvinyl polymer synthesized in an ethyl acetate/cyclohexane mixture | 0.1 | 0.1 | — | — |
| Cetyl palmitate (fatty substance a) | 2 | 2 | — | — |
| Glycerol | 5 | 1 | — | — |
| Cationic cellulose ether | — | — | — | 0.2 |
| Oxyethylenated oleyl alcohol (10 OE) (ethoxylated fatty alcohol b) | 1 | 1 | — | — |
| Oxyethylenated (20 OE) oleyl alcohol (ethoxylated fatty alcohol b) | 4 | 4 | — | — |
| Oxyethylenated decyl alcohol (5 OE) (ethoxylated alcohol b) | 1.2 | 0.9 | — | — |
| Oxyethylenated stearyl alcohol (2 OE) (ethoxylated fatty alcohol b) | — | — | 0.1 | 1.13 |
| Oxyethylenated stearyl alcohol (20 OE) (ethoxylated fatty alcohol b) | — | — | 0.1 | 3.88 |

| Ingredients | | | | |
|---|---|---|---|---|
| Cocoylbetaine as an aqueous solution | — | — | 10 | — |
| (50/50 $C_8/C_{10}$)Alkyl polyglucoside (2) as a buffered aqueous 60% solution | — | — | — | 4 |
| Oxyethylenated (60 OE) cetylstearyl ($C_{16}/C_{18}$) alcohol ether of myristyl glycol (ethoxylated fatty alcohol b) | 0.01 | 0.01 | — | — |
| Oxyethylenated sorbitan monolaurate (4 OE) | — | — | — | 2.4 |
| Sodium lauryl ether sulfate (2.2 OE) as an aqueous solution | — | — | 2.5 | — |
| Hydroxyethylcellulose | — | — | 2.5 | — |
| Sequestrant | 0.2 | 0.2 | 0.2 | 0.2 |
| Reducing agent | 0.22 | 0.22 | 0.22 | 0.22 |
| Fragrance | — | — | — | 0.72 |
| Deionized water | qs 100 | qs 100 | qs 100 | qs 100 |

| Ingredients | A9 | A10 | A11 |
|---|---|---|---|
| Liquid petroleum jelly (fatty substance a) | 4 | 60 | 50 |
| Oxyethylenated (40 OE) hydrogenated castor oil (fatty substance a) | — | 1 | — |
| 2-(2,5-Diaminophenyl)ethanol sulfate (oxidation base c) | 1.58 | 1.58 | 1.58 |
| 6-Hydroxybenzomorpholine (coupler d) | 0.033 | 0.033 | 0.033 |
| 1-β-Hydroxyethyloxy-2,4-diamino-benzene dihydrochloride (coupler d) | 0.02 | 0.02 | 0.02 |
| 1,3-Dihydroxybenzene (resorcinol) (coupler d) | 0.67 | 0.67 | 0.67 |
| 1-Hydroxy-3-aminobenzene (coupler d) | 0.12 | 0.12 | 0.12 |
| Pure monoethanolamine (basifying agent e) | 4 | — | 5.4 |
| Powdered sodium metabisulfite | 0.5 | 0.5 | — |
| Sodium sulfite | — | — | 0.4 |
| Carboxyvinyl polymer synthesized in an ethyl acetate/cyclohexane mixture | — | — | 0.4 |
| Oxyethylenated (20 OE) and oxypropylenated (5 OP) cetyl alcohol (ethoxylated fatty alcohol b) | 20 | — | — |
| Oxyethylenated (2 OE) stearyl alcohol (ethoxylated fatty alcohol b) | — | 0.1 | — |
| Oxyethylenated (20 OE) stearyl alcohol (ethoxylated fatty alcohol b) | — | 0.1 | 2 |
| Cocoylbetaine as an aqueous solution | — | 10 | — |
| Cetylstearyl alcohol (50/50 $C_{16}/C_{18}$) (fatty substance a) | — | — | 2.5 |
| Diethylenetriaminepentaacetic acid, pentasodium salt, as a 40% aqueous solution | 2 | 2 | — |
| Disodium ethylenediaminetetraacetate dihydrate | — | — | 0.2 |
| Erythorbic acid (or D-isoascorbic acid) | 0.3 | — | — |
| Oleylamidopropyldimethylamine | 2.5 | — | — |
| Hydroxyethylcellulose | — | 2.5 | — |
| Oxyethylenated sorbitan monolaurate (4 OE) | — | — | 5 |
| Sodium lauryl ether sulfate (2.2 OE) as an aqueous solution | — | 2.5 | — |
| Protected oxyethylenated (10 OE) oleyl alcohol hydrogen phosphate | 0.5 | — | — |
| Vitamin C: L-ascorbic acid as a fine powder | — | 0.5 | 0.3 |
| Deionized water | qs | qs | qs |

Oxidizing Compositions B5 to B12:

| Ingredients | B5 | B6 | B7 | B8 |
|---|---|---|---|---|
| Sequestrant | 0.15 | 0.15 | — | 0.15 |
| 50% Hydrogen peroxide (200 vol. aqueous hydrogen peroxide solution) | 12 | 12 | 15 | 12 |
| Tin disodium hexahydroxide | 0.04 | 0.04 | — | 0.04 |
| Etidronic acid, tetrasodium salt, as a 30% aqueous solution | — | — | 0.2 | — |
| Tetrasodium pyrophosphate decahydrate | 0.03 | 0.03 | 0.04 | 0.03 |
| Sodium salicylate | — | — | 0.035 | — |
| Liquid petroleum jelly (fatty substance a) | 20 | 20 | — | 20 |
| Poly[(dimethyliminio)-1,3-propanediyl(dimethyliminio)-1,6-hexanediyl dichloride] as an aqueous solution at 60% | 0.25 | 0.25 | — | 0.25 |
| Polydimethyldiallylammonium chloride at 40% in water, non-stabilized | 0.5 | 0.5 | — | 0.5 |
| Dimethyldiallylammonium chloride/acrylic acid copolymer (80/20) as a protected aqueous solution | — | — | 0.74 | — |
| Glycerol | 0.5 | 0.5 | 4 | 0.5 |
| Cetylstearyl alcohol (30/70 $C_{16}/C_{18}$) (fatty substance a) | 6 | 6 | — | 6 |
| Oxyethylenated (20 OE) cetylstearyl alcohol (ethoxylated fatty alcohol b) | 5 | 5 | — | 5 |
| (50/50 $C_8/C_{10}$)Alkyl polyglucoside (2) as a buffered aqueous 60% solution | — | — | 3 | — |
| Protected oxyethylenated (4 OE) rapeseed acid amide | 1.3 | 1.3 | — | 1.3 |
| Vitamin E: DL-α-tocopherol | 0.1 | 0.1 | — | 0.1 |

| Ingredients | B9 | B10 | B11 |
|---|---|---|---|
| Diethylenetriaminepentaacetic acid, pentasodium salt as an aqueous 40% solution | 0.15 | | 0.15 |
| 50% Hydrogen peroxide (200 vol. aqueous hydrogen peroxide solution) | 15 | 6 | 12 |
| Disodium tin hexahydroxide | 0.04 | | 0.04 |
| Etidronic acid, tetrasodium salt, as a 30% aqueous solution | | 0.2 | |

| | | | |
|---|---|---|---|
| Tetrasodium pyrophosphate decahydrate | 0.03 | 0.04 | 0.03 |
| Sodium salicylate | | 0.035 | |
| Liquid petroleum jelly (fatty substance a) | 35 | | 20 |
| Poly[(dimethyliminio)-1,3-propanediyl(dimethyliminio)-1,6-hexanediyl dichloride] as an aqueous solution at 60% | 0.25 | | 0.25 |
| Polydimethyldiallylammonium chloride at 40% in water, non-stabilized | 0.5 | | 0.5 |
| Dimethyldiallylammonium chloride/acrylic acid copolymer (80/20) as a protected aqueous solution | | 0.74 | |
| Glycerol | 0.5 | 4 | 0.5 |
| Cetylstearyl alcohol (30/70 $C_{16}/C_{18}$) (fatty substance a) | 6 | | 6 |
| Oxyethylenated (20 OE) stearyl alcohol (ethoxylated alcohol b) | 5 | | 5 |
| (50/50 $C_8/C_{10}$)Alkyl polyglucoside (2) as a buffered 60% aqueous solution | | 3 | |
| Protected oxyethylenated (4 OE) rapeseed acid amide | 1.3 | | 1.3 |
| Vitamin E: DL-α-tocopherol | 0.1 | | 0.1 |

The dye compositions A5 to A11 are mixed with the corresponding oxidizing formulae B5 to B11 in proportions of 1 part of Ai per 1 part of Bi.

The mixtures Ai+Bi obtained are then applied to 90% grey hair. The "mixture/lock" bath ratio is 10/1 (g/g). The leave-on time is 35 minutes at 27° C.

After the leave-on time, the hair is rinsed with clear water and a shampoo is applied.

After drying, a light chestnut-brown shade of good strength and coverage is obtained on the hair in all the cases.

The invention claimed is:

1. A composition for dyeing keratin fibers, comprising:
   a) at least one fatty substance;
   b) at least one compound chosen from alkyl(poly)glucoside nonionic surfactants, oxyethylenated $C_8$ to $C_{30}$ fatty acid esters of sorbitan, and combinations thereof;
   c) at least one oxidation base chosen from (2,5-diaminophenyl)ethanol and acid salts thereof, solvates thereof, and hydrates thereof;
   d) optionally at least one coupler;
   e) optionally at least one basifying agent; and
   f) at least one chemical oxidizing agent;
   wherein the fatty substance content represents at least about 20% by weight, relative to the total weight of the composition.

2. The composition according to claim 1, wherein the fatty substance is present in an amount ranging from about 30% to about 60% by weight, relative to the total weight of the composition.

3. The composition according to claim 1, wherein the fatty substance is chosen from $C_6$-$C_{16}$ hydrocarbons, hydrocarbons containing more than 16 carbon atoms, non-silicone oils of animal origin, plant oils of triglyceride type, synthetic triglycerides, fluoro oils, fatty alcohols, esters of fatty acids and/or of fatty alcohols other than triglycerides, plant waxes, non-silicone waxes, and silicones.

4. The composition according to claim 1, wherein the fatty substance is liquid at room temperature and at atmospheric pressure.

5. The composition according to claim 4, wherein the fatty substance is non-silicone.

6. The composition according to claim 1, wherein b) represents at least one alkyl(poly)glucoside nonionic surfactant chosen from the compounds represented by formula (I) below:

$$R_1O\text{—}(R_2O)_t(G)_v \quad \text{(I)}$$

wherein:
R$_1$ represents a saturated or unsaturated, linear or branched alkyl group comprising from about 8 to 24 carbon atoms, or an alkylphenyl group in which the linear or branched alkyl group comprises from 8 to 24 carbon atoms,
R$_2$ represents an alkylene group comprising from about 2 to 4 carbon atoms,
G represents a saccharide unit comprising from 5 to 6 carbon atoms,
t denotes a value ranging from 0 to 10, and
v denotes a value ranging from 1 to 15.

7. The composition according to claim 1, wherein b) represents at least one oxyethylenated $C_8$ to $C_{30}$ fatty acid ester of sorbitan chosen from oxyethylenated derivatives of $C_{8-30}$ fatty acid monoesters and polyesters of sorbitan containing from 1 to 50 ethylene oxide units, and oxyethylenated derivatives of $C_{12-24}$ fatty acid monoesters and polyesters of sorbitan containing from 4 to 20 ethylene oxide units.

8. The composition according to claim 1, wherein b) represents at least one oxyethylenated $C_8$-$C_{30}$ fatty acid ester of sorbitan chosen from oxyethylenated derivatives of saturated $C_{12-24}$ fatty acid monoesters and polyesters, and sorbitan monolaurate oxyethylenated with 4 OE.

9. The composition according to claim 1, wherein b) is present in an amount ranging from about 0.1% to about 20% by weight, relative to the total weight of the composition.

10. The composition according to claim 1, wherein the oxidation base c) is present in an amount ranging from about 0.0001% to about 20% by weight, relative to the total weight of the composition.

11. The composition according to claim 1, further comprising at least one coupler d) chosen from meta-phenylenediamines, meta-aminophenols, meta-diphenols, naphthalene-based couplers, heterocyclic couplers; addition salts thereof; and combinations thereof.

12. The composition according to claim 1, further comprising at least one basifying agent e) chosen from inorganic basifying agents, organic basifying agents, hybrid basifying agents, aqueous ammonia, alkali metal carbonates or bicarbonates, sodium carbonate, sodium bicarbonate, potassium carbonate, potassium bicarbonate, sodium hydroxide, potassium hydroxide, organic amines, alkanolamines, oxyethylenated and/or oxypropylenated ethylenediamines, amino acids, compounds represented by formula (VII), and mixtures thereof:

wherein in formula (VII):
W is a compound chosen from a divalent $C_1$-$C_6$ alkylene radical optionally substituted with at least one hydroxyl group, and a $C_1$-$C_6$ alkyl radical, wherein W is optionally interrupted by at least one heteroatom; and
R$_x$, R$_y$, R$_z$, R$_t$, which may be identical or different, each represent a hydrogen atom, a $C_1$-$C_6$ alkyl or $C_1$-$C_6$ hydroxyalkyl radical, or a $C_1$-$C_6$ amino alkyl radical.

13. The composition according claim 12, wherein e) is chosen from alkanolamines, monoethanolamine, and amino acids in neutral or ionic form.

14. The composition according to claim 1, wherein f) is hydrogen peroxide.

15. A process for dyeing keratin fibers, in the method comprising applying to the fibers a composition comprising:
- a) at least one fatty substance;
- b) at least one compound chosen from alkyl(poly)glucoside nonionic surfactants, oxyethylenated C8 to C30 fatty acid esters of sorbitan, and combinations thereof;
- c) at least one oxidation base chosen from (2,5-diaminophenyl)ethanol and acid salts thereof, solvates thereof, and hydrates thereof;
- d) optionally at least one coupler;
- e) optionally at least one basifying agent; and
- f) at least one chemical oxidizing agent;
- wherein the fatty substance content represents at least about 20% by weight, relative to the total weight of the composition.

16. The process according to claim 15, wherein the composition is obtained by mixing at least two compositions.

17. The process according to claim 15, wherein the composition is derived from the mixing of compositions (A) and (B):
- wherein composition (A) comprises:
  - at least one oxidation base c),
  - at least one coupler d), and
  - optionally at least one basifying agent e);
- wherein composition (B) comprises:
  - at least one chemical oxidizing agent f);
- wherein at least one of the compositions (A) and (B) comprises:
  - at least one fatty substance, and
  - at least one compound chosen from alkyl(poly)glucoside nonionic surfactants, oxyethylenated $C_8$-$C_{30}$ fatty acid esters of sorbitan b), and combinations thereof; and
- wherein the fatty substance content of the composition resulting from the mixing of compositions (A) and (B) is at least 20% by weight, relative to the total weight of the composition.

18. The process according to claim 15,
- wherein the composition is derived from the mixing of three compositions, and
- wherein the three compositions are aqueous or at least one of the compositions is anhydrous.

19. The process according to claim 18,
- wherein the composition is derived from the mixing of two aqueous compositions (B') and (C') and an anhydrous composition (A'),
- wherein the anhydrous composition (A') comprises at least one fatty substance,
- wherein composition (B') comprises at least one coupler d),
- wherein composition (C') comprises at least one chemical oxidizing agent f),
- wherein optionally at least one basifying agent e) is included in compositions (A') and/or (B');
- wherein at least one compound b) chosen from alkyl (poly)glucoside nonionic surfactants, oxyethylenated $C_8$-$C_{30}$ fatty acid esters of sorbitan, and combinations thereof is included in at least one of the compositions (A'), (B') or (C'); and
- wherein the fatty substance content of the composition resulting from the mixing of compositions (A'), (B') or (C') is at least 20% by weight, relative to the total weight of the composition.

20. A multi-compartment device comprising at least two compartments chosen from:

I:
- i) a first compartment containing composition (A) comprising:
  - at least one oxidation base c) chosen from (2,5-diaminophenyl)ethanol and acid salts thereof, solvates thereof, and hydrates thereof,
  - at least one coupler d), and
  - optionally at least one basifying agent e); and
- ii) at least a second compartment containing composition (B) comprising:
  - at least one chemical oxidizing agent f);
- wherein at least one of the compositions (A) and (B) comprises:
  - at least one fatty substance, and
  - at least one compound chosen from alkyl(poly)glucoside nonionic surfactants, oxyethylenated $C_8$-$C_{30}$ fatty acid esters of sorbitan b), and combinations thereof;
- wherein the compositions of the compartments are intended to be mixed before application to give a composition after mixing of (A)+(B) in which the amount of fatty substance represents at least 20% by weight, relative to the total weight of the composition resulting from mixing of (A)+(B); or:

I':
- i) a first compartment containing anhydrous composition (A') comprising at least one fatty substance;
- ii) a second compartment containing a cosmetic composition (B') comprising at least one coupler d); and
- iii) at least a third compartment containing composition (C') comprising at least one chemical oxidizing agent f);
- wherein optionally at least one basifying agent e) is included in compositions (A') and/or (B');
- wherein at least one compound b) chosen from alkyl (poly)glucoside nonionic surfactants, oxyethylenated $C_8$-$C_{30}$ fatty acid esters of sorbitan, and combinations thereof is included in at least one of the compositions (A'), (B') or (C'); and
- wherein the compositions of the compartments are intended to be mixed before application to give a composition after mixing of (A')+(B')+(C') in which the amount of fatty substance represents at least 20% by weight, relative to the total weight of the composition resulting from mixing of (A')+(B')+(C').

* * * * *